US009677592B2

(12) United States Patent
Bernhardt

(10) Patent No.: US 9,677,592 B2
(45) Date of Patent: Jun. 13, 2017

(54) WITNESS ENABLED FASTENERS AND RELATED SYSTEMS AND METHODS

(71) Applicant: The Boeing Company, Chicago, IL (US)

(72) Inventor: Roger D. Bernhardt, O'Fallon, MO (US)

(73) Assignee: The Boeing Company, Chicago, IL (US)

( * ) Notice: Subject to any disclaimer, the term of this patent is extended or adjusted under 35 U.S.C. 154(b) by 172 days.

(21) Appl. No.: 14/531,835

(22) Filed: Nov. 3, 2014

(65) Prior Publication Data

US 2016/0123369 A1    May 5, 2016

(51) Int. Cl.
| F16B 31/02 | (2006.01) |
| G01L 1/24 | (2006.01) |
| G01L 5/24 | (2006.01) |
| G01L 5/00 | (2006.01) |
| G01N 21/64 | (2006.01) |

(52) U.S. Cl.
CPC ............... *F16B 31/02* (2013.01); *G01L 1/24* (2013.01); *G01L 5/0004* (2013.01); *G01L 5/24* (2013.01); *G01L 5/243* (2013.01); *G01N 2021/6439* (2013.01)

(58) Field of Classification Search
CPC .... G01L 3/12; G01L 3/1421; G01N 2011/008
USPC ............... 73/761, 862.08, 862.324
See application file for complete search history.

(56) References Cited

U.S. PATENT DOCUMENTS

| 3,799,108 A * | 3/1974 | Mosow ................. F16B 31/02 116/212 |
| 3,987,668 A * | 10/1976 | Popenoe .............. F16B 31/025 116/212 |
| 6,204,771 B1 * | 3/2001 | Ceney .................. F16B 31/025 250/559.19 |
| 6,629,055 B2 * | 9/2003 | McGee ............... B25B 23/1425 702/113 |
| 7,287,902 B2 | 10/2007 | Safai et al. |
| 7,434,480 B2 | 10/2008 | Georgeson et al. |
| 8,024,979 B2 * | 9/2011 | Clarke ................. F16B 31/025 73/760 |
| 8,555,755 B2 * | 10/2013 | Cattaneo ............ B25B 23/0035 73/761 |
| 8,720,278 B1 | 5/2014 | Toivola et al. |
| 2008/0204752 A1 | 8/2008 | Dorvee et al. |
| 2009/0173161 A1 * | 7/2009 | Kibblewhite ........... G01L 1/255 73/761 |

* cited by examiner

*Primary Examiner* — Max Noori
(74) *Attorney, Agent, or Firm* — Kolisch Hartwell, P.C.

(57) ABSTRACT

A fastening device may include a first member configured for forceful engagement with a second member. The first member may include a sensor configured to emit at least a first photo-luminescent signal to a detector when at least a predetermined first torque level is applied to the first member when the first and second members are engaged.

11 Claims, 7 Drawing Sheets

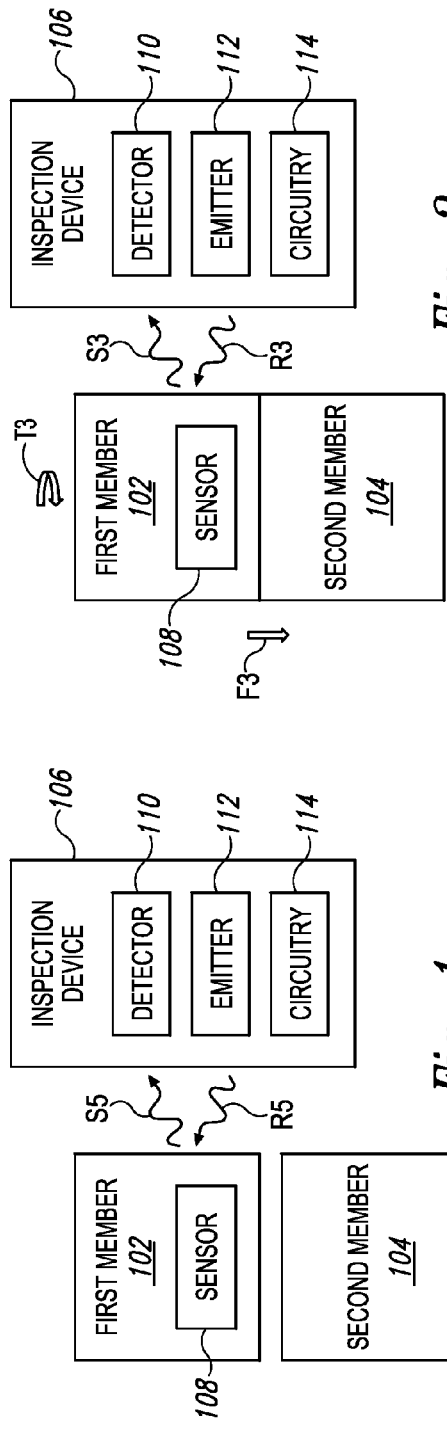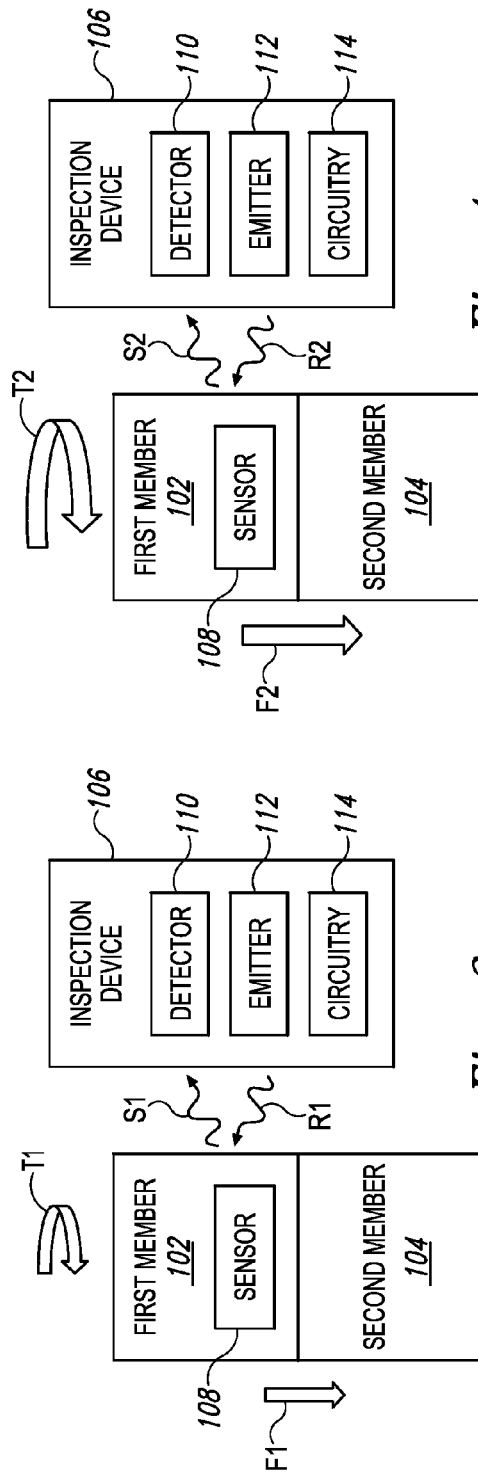

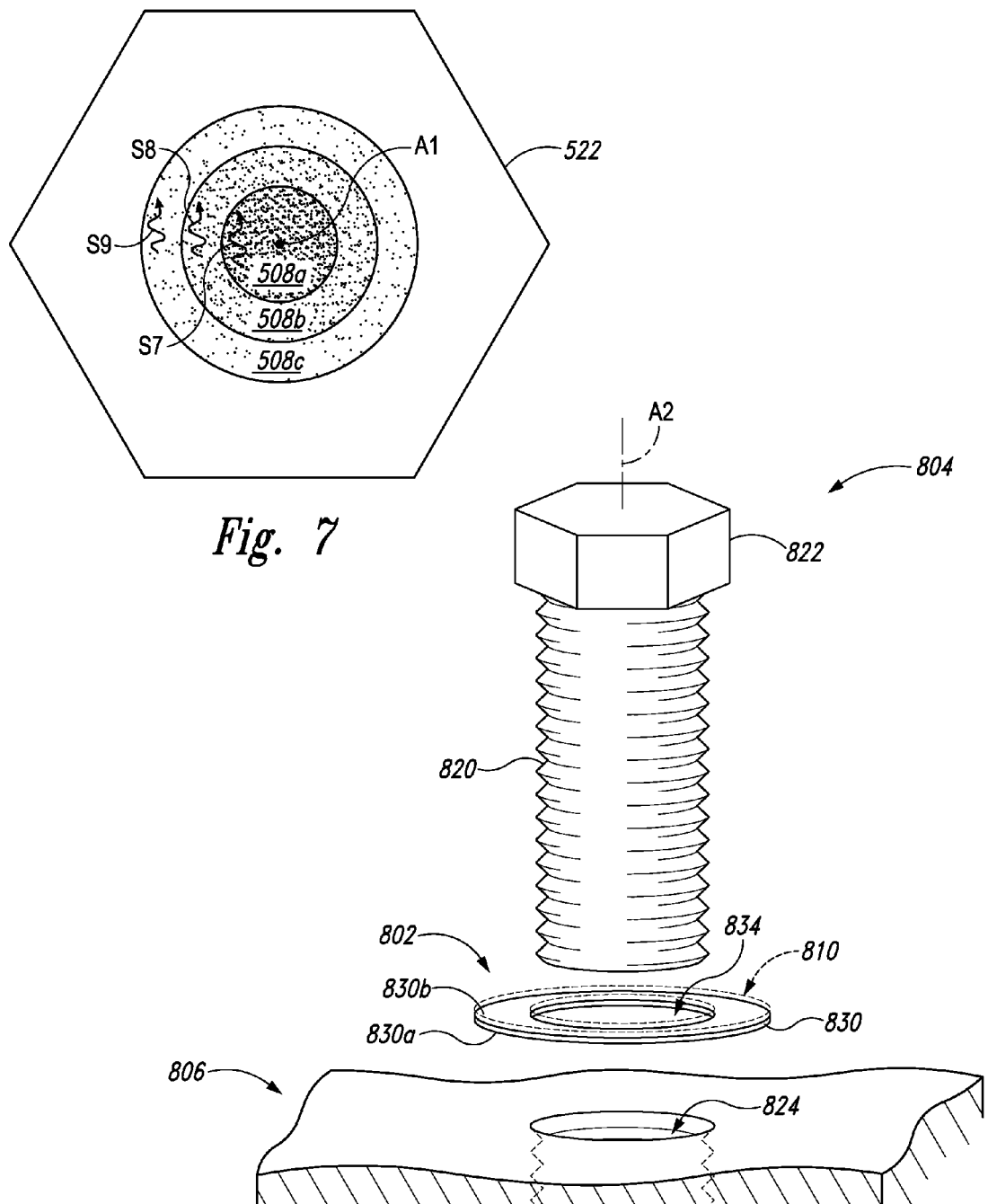

WITNESS ENABLED FASTENERS AND
RELATED SYSTEMS AND METHODS

FIELD

This disclosure relates to fasteners. More specifically, the disclosed embodiments relate to systems and methods for indicating a level of force on a fastener.

INTRODUCTION

Generally, a fastener is a hardware device that mechanically joins two or more objects, sometimes temporarily. For example, a bolt is one type of fastener, which in some cases has a threaded shaft and a head. The bolt and a second object, such as a nut or a base, can be mechanically joined by threading the threaded shaft into a complimentarily threaded hole in the second object. Typically, one or more other objects are disposed between the head and the second object. In such cases, mechanically joining the bolt and the second object may clamp the one or more other objects between the head and the second object.

In some situations, it may be desirable to know when a fastener is under-tightened, over-tightened, and/or improperly seated. For example, if a bolt is under-tightened into the second object, then the one or more other objects may not be suitably clamped between the head and the second object. Whereas if the bolt is over-tightened, then the shaft, the second object, and/or the one or more other objects clamped there between may become damaged. Similarly, improperly seating the bolt in the hole may damage both the shaft and the second object.

Torque wrenches exist which include a torque setting which allow a head of a bolt to be torqued to a predetermined level associated with the torque setting. However, various problems are associated with such devices. For example, torque wrenches generally do not indicate to a user when a shaft of the bolt is improperly seated (e.g., cross-threaded) in the second object. Further, when using a torque wrench to check a previously tightened fastener, the torque wrench is generally incapable of determining whether the fastener has been torqued past the predetermined level without increasing the torque setting, which if so increased, would likely cause further damage. Moreover, testing a fastener with a torque wrench generally requires mechanical engagement of the torque wrench with the fastener, resulting in significant torque testing times.

Accordingly, there exists a need for improved apparatuses, and/or related systems and/or methods for determining torque (or other forces) on a fastener.

SUMMARY

Disclosed herein are various examples of apparatuses, methods and systems, which may address the above mentioned problems, among others.

In one example, a fastening device may include a first member configured for forceful engagement with a second member. The first member may include a sensor comprising a fluorescent dye embedded in a polymer. The fluorescent dye may have a property that changes as a function of force applied to the first member for emission of a first photo-luminescent signal to a detector when at least a predetermined first torque level is applied to the first member when the first and second members are engaged. In some embodiments, the first photo-luminescent signal may correspond with a characterizing wavelength of a first photon emitted from the sensor in response to absorption of a second photon by the sensor. The characterizing wavelength of the first photon may be shifted as compared to a characterizing wavelength of the second photon for producing a color change.

In another example, a method may comprise engaging a first member with a second member. The first member may include a sensor configured to emit a first photo-luminescent signal indicating a desired predetermined level of torque applied to the first member when the first and second members are engaged. The method may further comprise torqueing the first member relative to the second member when the first and second members are engaged such that the sensor emits the first photo-luminescent signal.

In another example, a method may comprise receiving with a detector, a first photo-luminescent signal from a sensor included in a first member as the first member is being forcefully engaged with a second member. The first photo-luminescent signal may indicate a first level of torque applied to the first member. The first level of torque may be associated with the forceful engagement of the first member with the second member.

In another example, a system may comprise a fastener and an inspection device. The fastener may include a first member configured for forceful engagement with a second member. The first member may include a sensor configured to emit a first photo-luminescent signal. The first photo-luminescent signal may indicate at least a first level of torque applied to the first member when the first and second members are engaged. The inspection device may be configured to receive the first photo-luminescent signal from the sensor. In some embodiments, the inspection device may be configured to determine the first level of torque by comparing spectral information included in the first photo-luminescent signal against a standard.

In another example, a tool may comprise a tightening device and an inspection device. The tightening device may be configured to apply force to a first member engaged with a second member. The inspection device may be coupled to the tightening device. The inspection device may be configured to receive a photo-luminescent signal emitted from the first member. The photo-luminescent signal may indicate a level of force applied to the first member by the tightening device.

In another example, a washer may comprise a structural member and a sensor. The structural member may have first and second opposing surfaces through which a central aperture may be defined for receiving a shaft of a fastening member. The sensor may be coated on one or more of the first and second surfaces. The sensor may include a layer of polymer embedded with a fluorescent dye. The fluorescent dye may have a property that changes as a function of force applied to the structural member for emission of a photo-luminescent signal indicative of a level of force transmitted to the structural member by a head portion of the fastening member and another member into which the shaft extends opposite the head portion relative to the structural member.

The present disclosure provides various apparatuses, systems, and methods associated with indicating stress, such as torque or other forces, on a fastener. In some embodiments, an apparatus, system, and/or method may enable monitoring and/or testing of torque (or other force) levels on a fastener via reception of a photo-luminescent signal from a sensor included in the fastener.

Features, functions, and advantages may be achieved independently in various embodiments of the present disclosure, or may be combined in yet other embodiments, further details of which can be seen with reference to the following description and drawings.

BRIEF DESCRIPTION OF THE DRAWINGS

FIG. 1 is a general block diagram of an exemplary system including first and second members, and an inspection device, with a sensor included in the first member emitting a baseline photo-luminescent signal to a detector included in the inspection device.

FIG. 2 is a general block diagram of the system of FIG. 1 showing the first and second members forcefully engaged, and the sensor emitting an "under-tightened" photo-luminescent signal to the detector.

FIG. 3 is a general block diagram similar to FIG. 2, but showing the first and second members further forcefully engaged, and the sensor emitting an "appropriately-tightened" photo-luminescent signal to the detector.

FIG. 4 is a general block diagram similar to FIG. 3, but showing the first and second members even further forcefully engaged, and the sensor emitting an "over-tightened" photo-luminescent signal to the detector.

FIG. 7 is a top view of the first member of FIG. 6 from the perspective of the detector, depicting the sensor emitting a plurality of photo-luminescent signals.

FIG. 8 is a semi-schematic perspective view of a bolt, a washer having a surface coated with a sensor, and a third member including a threaded aperture for receiving a threaded shaft of the bolt.

DESCRIPTION

Overview

Various embodiments are described below and illustrated in the associated drawings. Unless otherwise specified, an embodiment and/or its various components may, but are not required to, contain at least one of the structure, components, functionality, and/or variations described, illustrated, and/or incorporated herein. Furthermore, the structures, components, functionalities, and/or variations described, illustrated, and/or incorporated herein in connection with the present teachings may, but are not required to, be included in other similar embodiments. The following description of various embodiments is merely exemplary in nature and is in no way intended to limit the disclosure, its application, or uses. Additionally, the advantages provided by the embodiments, as described below, are illustrative in nature and not all embodiments provide the same advantages or the same degree of advantages.

In some embodiments, two or more materials may be integrated into a fastener and/or substrate. The materials may be configured such that when proper fastening techniques are applied to the fastener (and/or substrate), properties of the materials change to indicate proper engagement and/or installation of the fastener (and/or substrate). For example, the fastener may include a split locknut. The split locknut may include a sensor, such as two segments having respective properties. When the two segments are fully engaged, the properties may blend (or otherwise interact) in such a fashion to turn green (or another color, or emit another signal) if properly installed, and red (or another color, or emit another signal) if over-tightened. In some examples, the sensor may turn yellow (or another color, or emit another signal) to indicate a condition where tightness (and/or engagement) is incomplete prior to and/or during installation. Overheating and/or galling of the fastener could create a "red" condition. External illumination for fluorescence may include an ultraviolet (UV) light emitter, an infrared (IR) light emitter, or any other suitable spectrally enhancing source (or emitter) of illumination, or combination thereof. For example, the sensor "turning green" may correspond to emission of a first photo-luminescent signal from the sensor in response to absorption of electromagnetic (EM) radiation emitted from the emitter.

EXAMPLES, COMPONENTS, AND ALTERNATIVES

The following examples describe selected aspects of exemplary apparatuses as well as related systems and/or methods. These examples are intended for illustration and should not be interpreted as limiting the entire scope of the present disclosure. Each example may include one or more distinct inventions, and/or contextual or related information, function, and/or structure.

Example 1

This example describes an illustrative system 100 including a first member 102, a second member 104, and an inspection device 106; see FIGS. 1-4.

Figure 5:
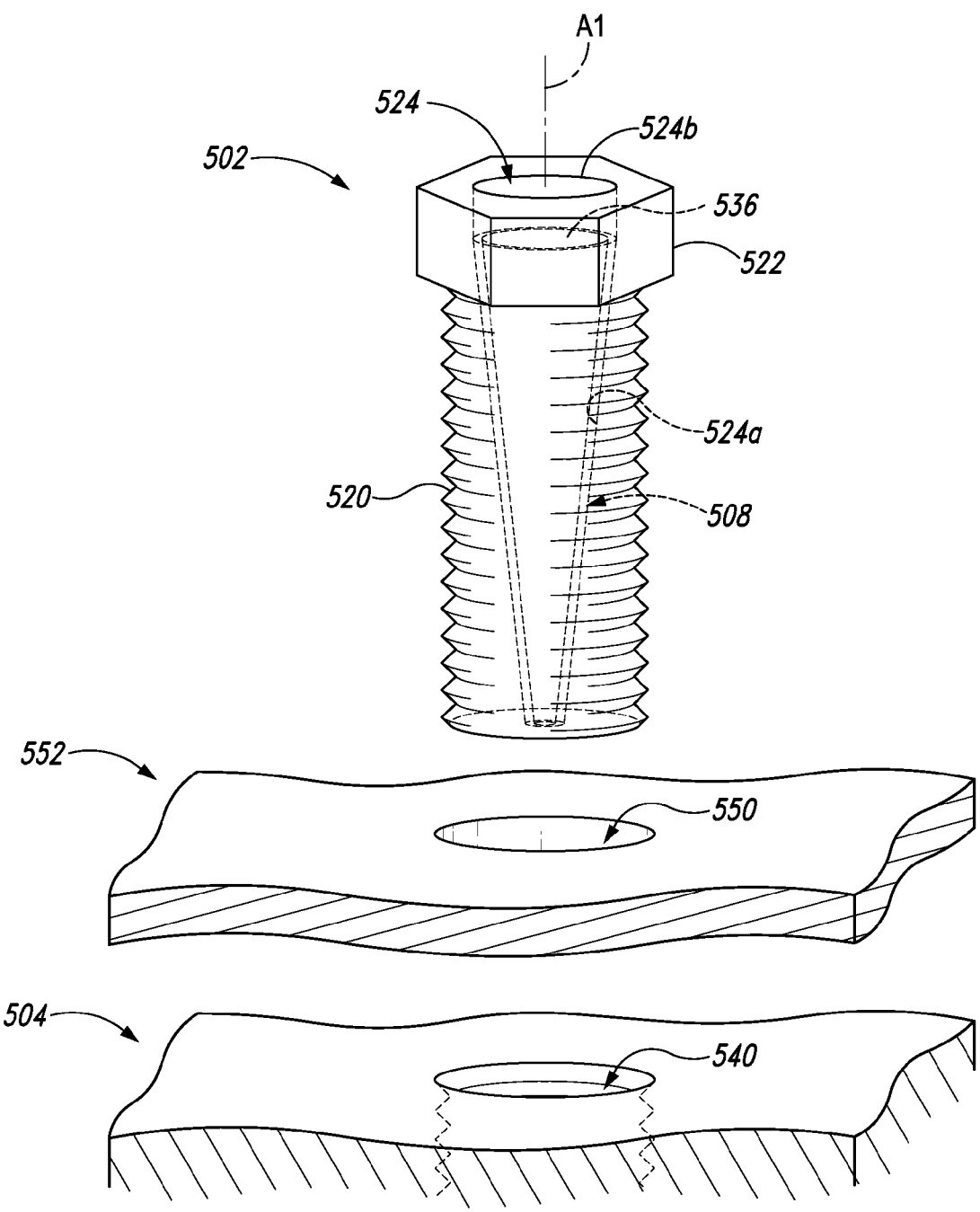
FIG. 5 is a semi-schematic perspective view of a first member (shown here as a bolt) having an internal channel coated with a sensor, and a second member having a threaded aperture for receiving the first member.
Figure 6:
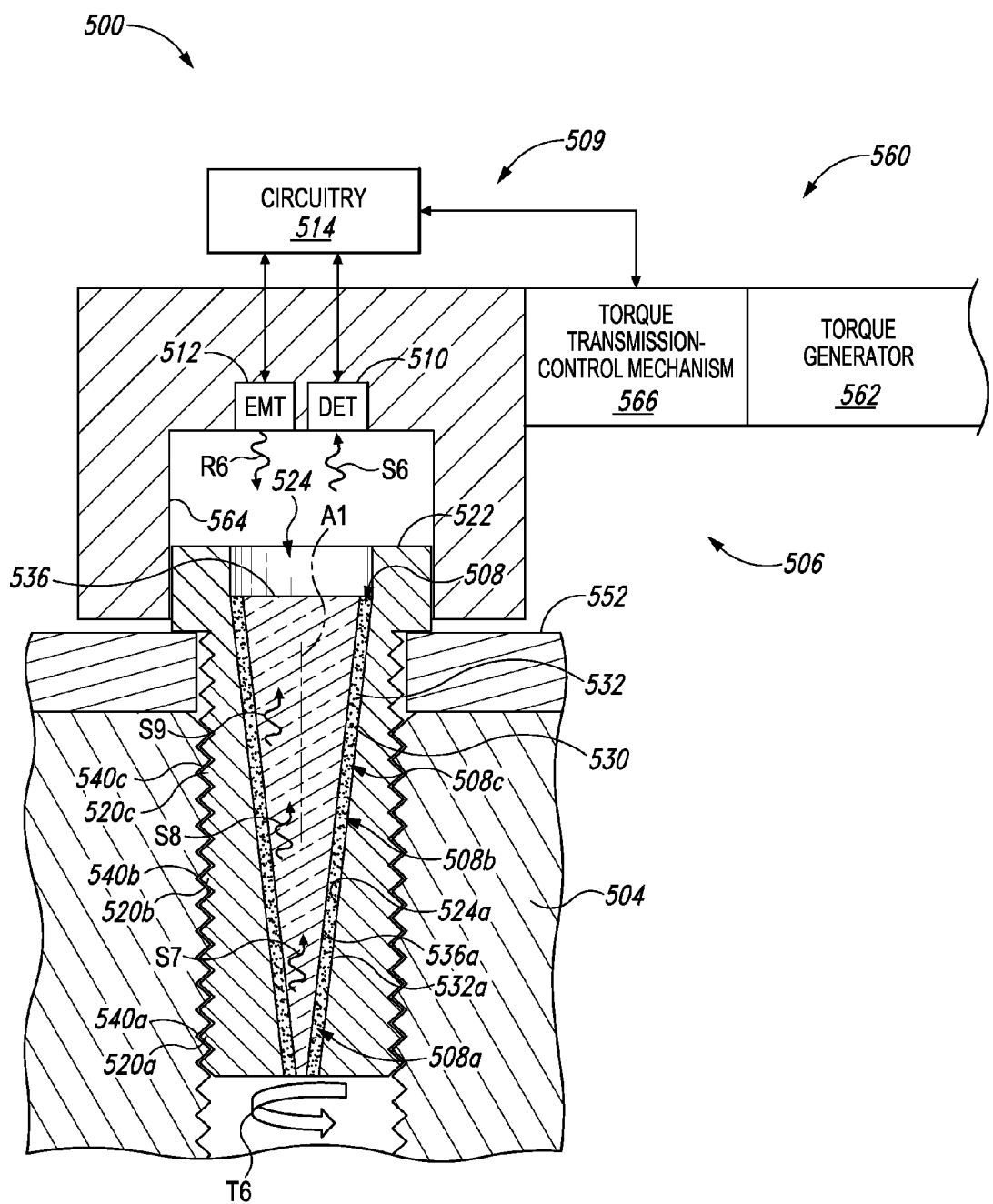
FIG. 6 is a semi-schematic cross-sectional view of the first and second members of FIG. 5 engaged with one another, and a tool including a tightening device and an inspection device, with the tightening device having a socket configured to apply a force (e.g., a torque) to the first member, and the inspection device including a detector for receiving a photo-luminescent signal from the sensor via the socket.
Figure 9:
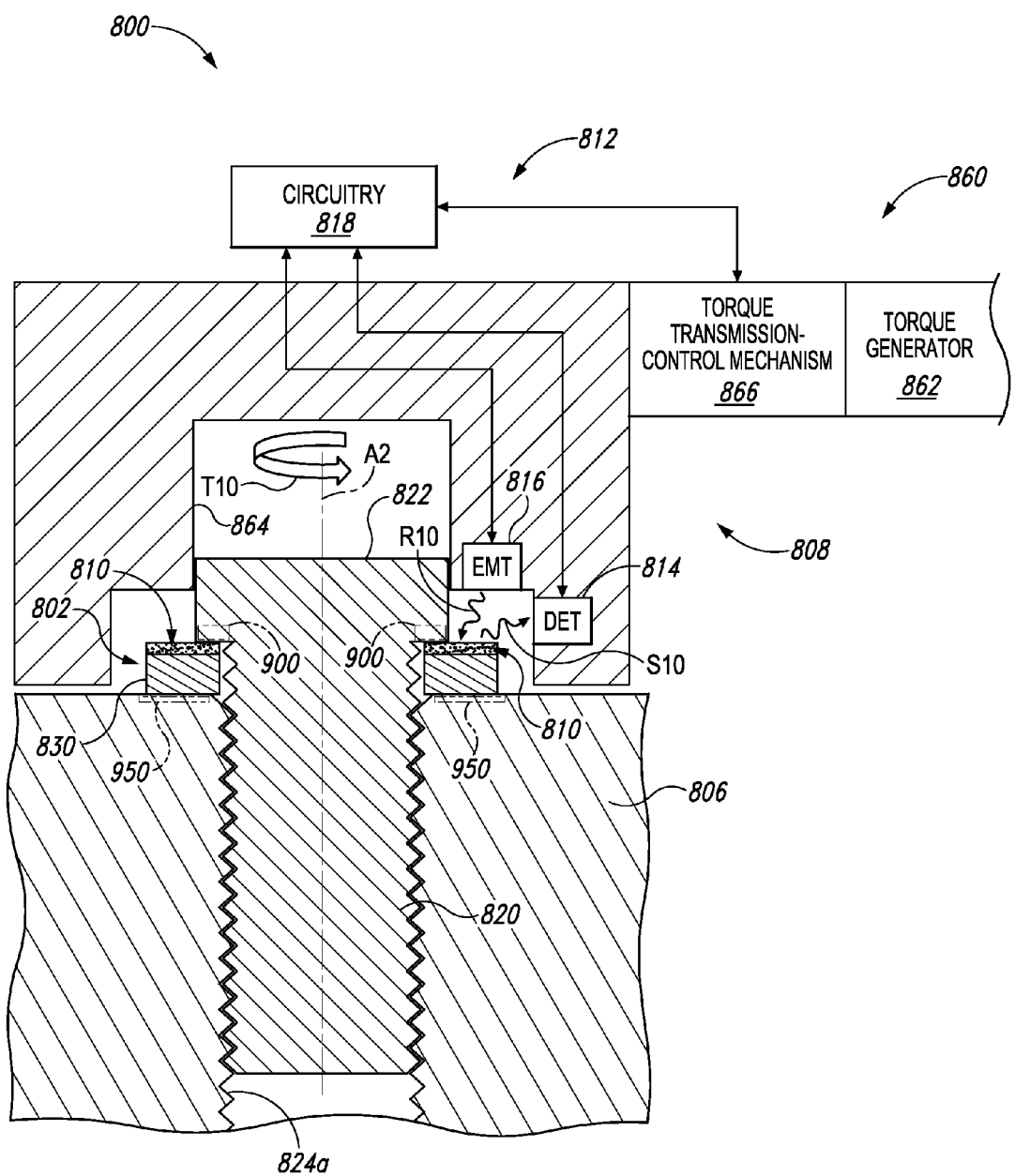
FIG. 9 is a semi-schematic cross-sectional view of the bolt, the washer, and the third member of FIG. 8 engaged with one another, and a tool similar to the tool of FIG. 6 but including an inspection device configured to receive a photo-luminescent signal from the sensor coated on the washer.

First member 102 may be configured for forceful engagement with second member 104. For example, first member 102 may include a bolt (e.g., as shown in FIGS. 5-7), a washer (e.g., as shown in FIGS. 8 and 9), a nut, a lock-nut (e.g., a nylon lock nut, or ny-lock), a base with a threaded aperture for receiving a shaft, a clamp, a rivet, a clip, and/or any other suitable fastening member configured for forceful engagement with another member. For example, if first member 102 includes a bolt, then second member 104 may include an aperture having threads with which a threaded shaft of the bolt may be forcefully engaged. Similarly, if first member 102 includes a washer, then second member 104 may include a bolt, a nut, and/or another base-type fastening member against which the washer may be forcefully engaged.

As shown in FIGS. 1-4, first member 102 may include a sensor 108. Sensor 108 may be configured to emit one or more photo-luminescent signals. The one or more photo-luminescent signals may respectively indicate one or more levels of force applied to first member 102, as will be described below in more detail. For example, in some embodiments, sensor 108 may comprise a fluorescent dye embedded in a polymer. The fluorescent dye may have a property that changes as a function of force applied to first member 102 for emission of the one or more photo-luminescent signals. Examples of such compositions are disclosed in U.S. Pat. No. 8,720,278, which is hereby incorporated by reference in its entirety for all purposes. In other embodiments, sensor 108 may include two or more reactants, and one or more predetermined force levels applied to first member 102 may be configured to bring two or more of those reactants into proximity with one another thereby forming one or more particulate sensor materials (or other suitable compositions) for emission of the one or more photo-luminescent signals in response to excitation (e.g., absorbed electromagnetic radiation). Examples of such particulate sensor materials are disclosed in U.S. Patent Application No. 2008/0204752, which is hereby incorporated by reference in its entirety for all purposes.

As shown, sensor 108 may be configured to emit a first photo-luminescent signal S1 (see FIG. 3). Signal S1 may indicate when a predetermined first level of force, such as a first torque level T1, is applied to first member 102 when members 102, 104 are engaged. For example, the first force level may correspond to a desired and/or appropriate level of force F1 for fastening together members 102, 104, which may be associated with torque level T1.

Additionally or alternatively, sensor 108 may be configured to emit a second photo-luminescent signal S2 (see FIG. 4). Signal S2 may indicate when a predetermined second level of force, such as a second torque level T2, is applied to first member 102 when members 102, 104 are engaged. For example, the second level of force may correspond to a predetermined undesirable and/or inappropriate level of force F2 for fastening together members 102, 104, which may be associated with torque level T2. In particular, second torque level T2 may correspond to an over-torqueing (or over-tightening) of first member 102 relative to (and/or onto, and/or into) second member 104. More specifically, second torque level T2 may be greater (e.g., in magnitude) than first torque level T1. In some embodiments, signal S2 may indicate that torque applied to first member 102 has exceeded torque level T1 by at least a threshold amount of torque. For example, the threshold amount may correspond to an amount of torque in excess of torque level T1 (e.g., level T2 may correspond to 110% of level T1, or other predetermined percentage, and the threshold amount may correspond to a difference between levels T2, T1, or fraction thereof) that may damage one or more of members 102, 104, and/or may result in a weakened or otherwise undesirable fastening interface between members 102, 104.

Additionally or alternatively, sensor 108 may be configured to emit a third photo-luminescent signal S3 (see FIG. 2). Signal S3 may indicate when a predetermined third level of force, such as a third torque level T3, is applied to first member 102 when members 102, 104 are engaged. The third level of force may correspond to an inappropriate third level of force F3 for fastening together members 102, 104. In particular, third torque level T3 may correspond to an under-torqueing (or under-tightening) of first member 102 relative to (and/or onto, and/or into) second member 104. More specifically, third torque level T3 may be less (e.g., in magnitude) than first torque level T1.

In some embodiments, first torque level T1 may be at least 3 foot-pounds (ft-lbs) or 4.1 Newton meters (Nm). However, depending upon various parameters of the application, such as material compositions (and/or characteristics thereof) of one or more of members 102, 104, first torque level T1 may be greater or less than 3 foot-pounds (4.1 Nm). For example, first torque level T1 may correspond to any one of torque levels in the following exemplary table, which may be suitable (and/or preselected) for a particular application.

| | | SAE Grade | | | | | | | |
|---|---|---|---|---|---|---|---|---|---|
| Bolt Diameter (in inches) | Threads per inch | 2 Torque if Dry (in ft-lbs) | 2 Torque if Oiled (in ft-lbs) | 5 Torque if Dry (in ft-lbs) | 5 Torque if Oiled (in ft-lbs) | 7 Torque if Dry (in ft-lbs) | 7 Torque if Oiled (in ft-lbs) | 8 Torque if Dry (in ft-lbs) | 8 Torque if Oiled (in ft-lbs) |
| 1/4 | 20 | 4 | 3 | 8 | 6 | 10 | 8 | 12 | 9 |
| 1/4 | 28 | 6 | 4 | 10 | 7 | 12 | 9 | 14 | 10 |
| 5/16 | 18 | 9 | 7 | 17 | 13 | 21 | 16 | 25 | 18 |
| 5/16 | 24 | 12 | 9 | 19 | 14 | 24 | 18 | 29 | 20 |
| 3/8 | 16 | 16 | 12 | 30 | 23 | 40 | 30 | 45 | 35 |
| 3/8 | 24 | 22 | 16 | 35 | 25 | 45 | 35 | 50 | 40 |
| 7/16 | 14 | 24 | 17 | 50 | 35 | 60 | 45 | 70 | 55 |
| 7/16 | 20 | 34 | 26 | 55 | 40 | 70 | 50 | 80 | 60 |
| 1/2 | 13 | 38 | 31 | 75 | 55 | 95 | 70 | 110 | 80 |
| 1/2 | 20 | 52 | 42 | 90 | 65 | 100 | 80 | 120 | 90 |
| 9/16 | 12 | 52 | 42 | 110 | 80 | 135 | 100 | 150 | 110 |
| 9/16 | 18 | 71 | 57 | 120 | 90 | 150 | 110 | 170 | 130 |
| 5/8 | 11 | 98 | 78 | 150 | 110 | 140 | 190 | 220 | 170 |
| 5/8 | 18 | 115 | 93 | 180 | 130 | 210 | 160 | 240 | 180 |
| 3/4 | 10 | 157 | 121 | 260 | 200 | 320 | 240 | 380 | 280 |
| 3/4 | 16 | 180 | 133 | 300 | 220 | 360 | 280 | 420 | 320 |
| 7/8 | 9 | 210 | 160 | 430 | 320 | 520 | 400 | 600 | 460 |
| 7/8 | 14 | 230 | 177 | 470 | 360 | 580 | 440 | 660 | 500 |
| 1 | 8 | 320 | 240 | 640 | 480 | 800 | 600 | 900 | 680 |
| 1 | 12 | 350 | 265 | 710 | 530 | 860 | 666 | 990 | 740 |

As such, emission of one or more of signals S1, S2, S3 by sensor 108 included in first member 102, may permit a user and/or a tool to monitor and/or test a force level (e.g., a torque level) applied to first member 102 (e.g., relative to second member 104) via an optical inspection (e.g., in a visual or non-visual spectrum) of first member 102. Such an optical inspection may permit the user and/or tool (or automated system) to more accurately and/or more efficiently monitor and/or test the force level on first member 102, particularly as compared to pre-existing methods that generally involve mechanically testing a force level on a fastener.

More specifically, inspection device 106 may include a detector (also referred to as collection optics) 110, an emitter (also referred to as illumination optics) 112, and circuitry 114. Detector 110 may be configured to receive signal S1 (and/or any of the other photo-luminescent signals from sensor 108). For example, detector 110 may include an electronic photo-detector. Examples of such detectors include photomultiplier tubes (PMTs), photodiodes, avalanche photodiodes, charge-coupled devices (CCDs), complementary metal-oxide-semiconductor (CMOS) devices, or the like. Accordingly, detector 110 may be a point detector or an imaging detector. In some embodiments, detector 110 may include a human eye, in which cases, detector 110 may not be included in inspection device 106.

Emitter 112 may be configured to emit electromagnetic (EM) radiation, such as EM radiation R1, R2, R3, toward sensor 108. In response to absorption of radiation R1, R2, R3, sensor 108 may emit respective photo-luminescent signals S1, S2, S3. For example, emitter 112 may be configured to illuminate sensor 108 with at least one beam of light (also termed radiation) produced by at least one light source, which may be included in emitter 112. Illumination also or alternatively may be described as irradiation, and a light source as a radiation source. Exemplary "light" sources include light-emitting diodes (LEDs), lasers, and so on. Each light source may be an excitation source configured to emit radiation at a particular wavelength or range of wavelengths. Further, each light source (or the light source) may (or may not be) configured to emit radiation having a specific (and/or different) spectral signature, to react with fluorophores (e.g., fluorescent dyes), which may be included in sensor 108, as described above. For example, the light source may include an LED, such as an IR or UV LED, configured to emit radiation with a peak amplitude at a specific frequency (e.g., radiation of a specific "color"). In some embodiments, the light source(s) may be configured to emit anisotropic radiation characterized by a specific polarization, which may comprise the spectral signature. Light from the light source(s) may be transmitted to sensor 108 via the illumination optics. For example, the illumination optics may modify the spectral signature of light emitted by each light source, such as by limiting the range of wavelengths used for illumination.

Detector (or collection optics or system) 110 may gather and detect light from sensor 108, such as light produced in response to illumination of sensor 108 by emitter (or illumination optics or system) 112. Illumination optics 112 and collection optics 110 each may include one or more optical elements that transmit light from each light source (e.g., if more than one) to sensor 108 or from sensor 108 to the detector(s). Accordingly, the illumination optics may define an optical path traveled by light from the light source(s) to sensor 108, and the collection optics may define an optical path traveled by light from sensor 108 to the detector(s). Each optical path may be branched or unbranched. If two or more light sources are used in illumination optics 112, then illumination optics 112 may combine beams from the light sources, such that radiation incident on sensor 108 is a combined beam from multiple light sources. In a combined beam, individual beams from the light sources overlap one another. If two or more detectors are used in collection optics 110, then collection optics 110 may spit collected light (e.g., emission light corresponding to the photo-luminescent signal) received from sensor 108, to send a portion of the collected light to each detector. In some cases, within a single detection unit, such as inspection device 106, the illumination optics may combine beams from multiple light sources, and the collection optics may distribute collected light between or among multiple detectors. Alternatively, in some embodiments, the illumination optics may combine beams, or the collection optics may split a collected beam, but not both.

An optical element can be any structure or device that collects, directs, and/or focuses light and/or selectively blocks undesirable light, among others. An optical element may function by any suitable mechanism, such as light refraction, reflection, diffraction, blocking, and/or filtering, among others. Exemplary optical elements include lenses, mirrors, gratings, prisms, filters, beam splitters, transmissive fibers (fiber optics), apertures, diffusers, or the like.

In some cases, illumination optics and/or collection optics may not be used in the inspection device. For example, a light beam from a light source may travel directly to sensor 108 without being transmitted by any interposed optical element(s). Alternatively, or in addition, light from sensor 108 (e.g., signal S1) may travel directly to a detector (e.g., a detector close to sensor 108) without being transmitted by any interposed optical element(s). In some embodiments, as described further above, the detector may include a human eye, in which cases, the photo-luminescent signal from sensor 108 may (or may not) be received from sensor 108 via inspection device 106.

Figure 12:
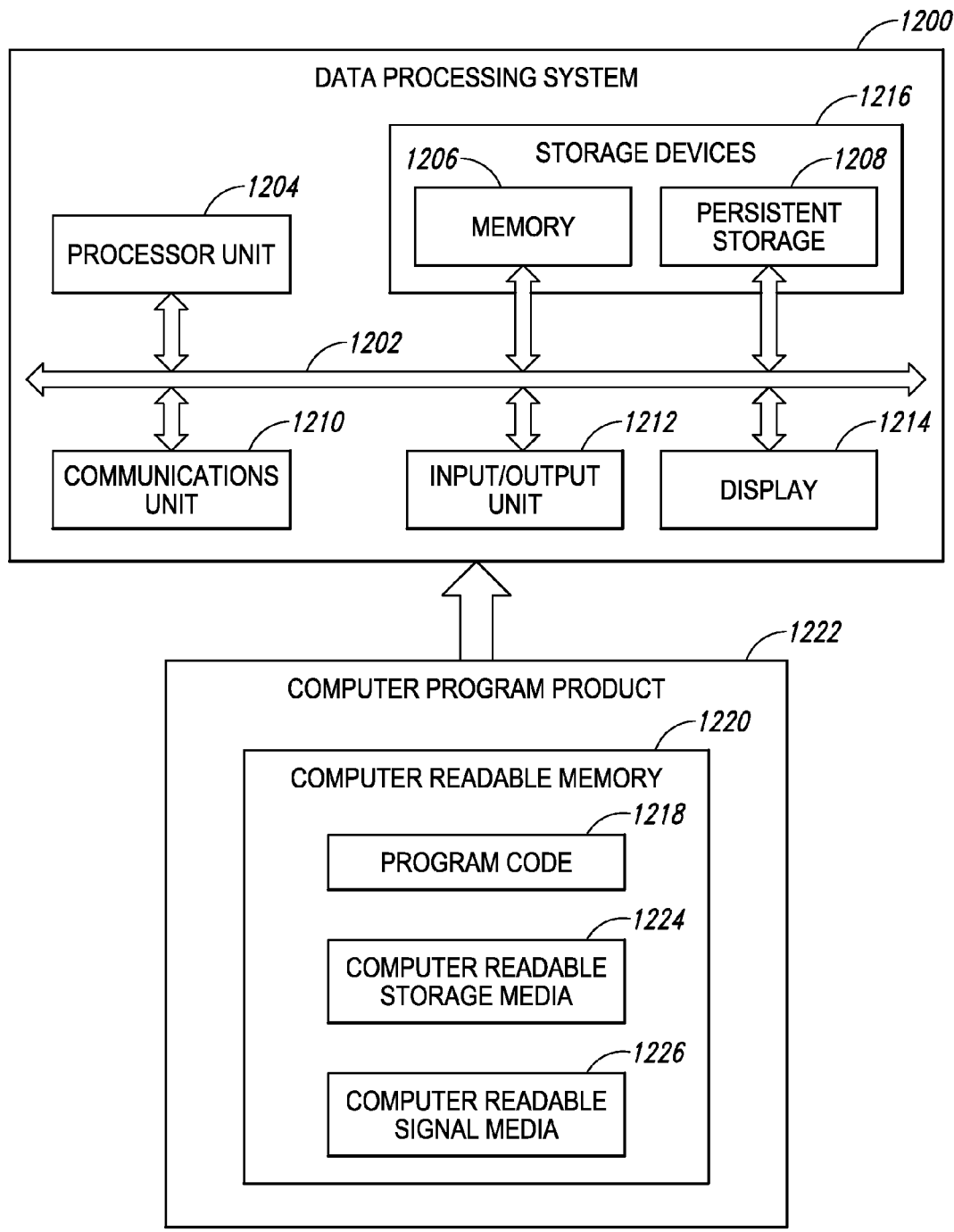
FIG. 12 is a schematic diagram of various components of an illustrative data processing system.

Circuitry 114 may include one or more components (and/or associated functionalities) of a data processing system, such as the one depicted and described with reference to FIG. 12. In some embodiments, circuitry 114 may be configured to determine whether a predetermined level of force (e.g., on first member 102) has or has not been reached and/or has or has not been exceeded based at least in part on reception of at least one of the photo-luminescent signals from sensor 108. For example, circuitry 114 may be configured to determine the force level associated with the respective signal by comparing the spectral signature (or spectral information associated therewith) of light emitted from emitter 112 to a spectral signature (or spectral information associated therewith) included in the at least one photo-luminescent signal received by detector 110, as will be described below in further detail.

In some embodiments, one or more components and/or associated functionalities of circuitry 114 may be included in detector 110. For example, detector 110 (e.g., including one or more data processing components and/or functionalities) may be configured to generate a user signal based on and indicative of the respective photo-luminescent signal received from sensor 108, and output the user signal to a user (e.g., a human or non-human user of inspection device 106). For example, the user signal may include an audible signal (e.g., a beep), a visual signal (e.g., a flashing light), a haptic signal (e.g., a tactile vibration or impulse), and/or another data signal, such as a digital signal (e.g., which may be utilized by an automated system). The user signal may indicate that a particular force level, such as torque level T1, on first member 102 relative to second member 104 has not yet been reached (e.g., corresponding to signal S3, torque level T3, and/or force level F3), has been reached (e.g., corresponding to signal S1, torque level T1, and/or force level F1), and/or has been exceeded (e.g., corresponding to signal S2, torque level T2, and/or force level F2).

In an exemplary operation of system 100, inspection device 106 may be used (e.g., by a user, and/or an automated or robotic system) to collect or receive a baseline photo-luminescent signal S5 from sensor 108, as is shown in FIG. 1. For example, emitter 112 may be configured (and/or operated via device 106) to emit EM radiation R5 toward sensor 108. In response to absorption of radiation R5, sensor 108 may emit signal S5. Signal S5 may indicate a level of force and/or torque on first member 102 when first member 102 is not engaged with second member 104, as is depicted in FIG. 1. For example, signal S5 may indicate a baseline internal stress (or force, or torque) of first member 102. In particular, the baseline internal force may correspond to an internal stress of first member 102 (and/or sensor 108).

In some embodiments, a previous baseline photo-luminescent signal may have been acquired by (or may be accessible by) inspection device 106, in which case inspection device 106 (e.g., circuitry 114) may compare signal S5 with the previous baseline signal to determine if the baseline internal stress associated with first member 102 has not exceeded a predetermined threshold (e.g., 110% of the previous baseline internal stress, or other tolerable percentage). For example, comparison of signal S5 with the previous baseline photo-luminescent signal (or data representative thereof) may permit circuitry 114 to determine whether first member 102 has been excessively over-torqued, or otherwise damaged, after collection of the previous baseline photo-luminescent signal, but before reception of signal S5 by detector 110. Accordingly, if circuitry 114 determines that first member 102 has been so damaged, then circuitry 114 may signal the user (e.g., via a user interface) and/or an automated system (e.g. a robotic system) that first member 102 is no longer suitable for being fastened to second member 104. In some embodiments, the user and/or the automated system may comprise an operator of system 100.

However, if circuitry 114 determines that the baseline internal stress of first member 102 has not been exceeded (e.g., is not presently exceeding) the predetermined threshold, then circuitry 114 may signal the operator indicating that first member 102 is in a suitable condition for being fastened with second member 104.

For example, if circuitry 114 signals the operator that the baseline internal stress of first member 102 has not exceeded the predetermined threshold, then the operator may engage first member 102 with second member 104, as is depicted in FIG. 2. When first and second members 102, 104 are engaged, the operator may torque first member 102 relative to second member 104, for example, resulting in (or with) torque level T3 and/or force level F3.

While (or after) torqueing first member 102, as depicted in FIG. 2, the operator may use inspection device 106. For example, the operator may operate inspection device 106 to emit radiation R3 toward sensor 108. Sensor 108 may absorb radiation R3. In response to absorption of radiation R3, sensor 108 may emit signal S3. Detector 110 may receive signal S3. Inspection device 106 may determine one or more of torque level T3 and force level F3 based at least in part on reception of signal S3 by detector 110. For example, circuitry 114 may be configured to determine one or more of torque level T3 and force level F3 by comparing signal S3 (e.g., spectral information associated therewith) against a standard, such as respective spectral information associated with one or more of radiation R3 and signal S5. Further, based at least in part on the determination by circuitry 114 of one more of torque level T3 and force level F3, circuitry 114 may emit a first user signal to the operator indicating that the torque applied to first member 102 (e.g., relative to second member 104) has not yet reached the predetermined appropriate application of torque (e.g., torque level T1) for fastening together members 102, 104. Accordingly, in response to reception of the first user signal, the operator may further forcefully engage (e.g., torque) first member 102 relative to second member 104.

For example, the operator may further forcefully engage first member 102 with second member 104 (e.g., may further torque first member 102 relative to second member 104) such that sensor 108 emits signal S1 (and/or ceases to emit signal S3). While (or after) torqueing first member 102, as depicted in FIG. 3, the operator may use inspection device 106. For example, the operator may operate inspection device 106 to emit radiation R1 toward sensor 108. Sensor 108 may absorb radiation R1. In response to absorption of radiation R1, sensor 108 may emit signal S1. Detector 110 may receive signal S1. Inspection device 106 may determine one or more of torque level T1 and force level F1 based at least in part on reception of signal S1 by detector 110. For example, circuitry 114 may be configured to determine one or more of torque level T1 and force level F1 by comparing signal S1 (e.g., spectral information associated therewith) against a standard, such as respective spectral information associated with one or more of radiation R1 and signal S5. Further, based at least in part on the determination by circuitry 114 of one more of torque level T1 and force level F1, circuitry 114 may emit a second user signal to the operator indicating that the torque applied to first member 102 (e.g., relative to second member 104) has reached the predetermined appropriate (and/or desirable) application of torque (e.g., torque level T1) for fastening together members 102, 104. Accordingly, in response to reception of the second user signal, the operator may cease applying force (e.g., torque) to first member 102 relative to second member 104.

In some cases, first member 102 may become overly forcefully engaged (e.g., overly torqued) relative to second member 104, as depicted in FIG. 4. For example, torque level T2 may be in excess of torque level T1 by the threshold amount. In one example, level T2 may correspond to 110% of level T1. Various non-limiting examples of embodiments of torque level T1 are shown in the table further above. In some embodiments, the threshold amount may be equal to a difference between levels T2, T1. For example, if level T1 corresponds to 10 ft-lbs, then level T2 may correspond to 11 ft-lbs, and the threshold amount may correspond to 1 ft-lb. However, in other embodiments, level T2 may be less than or greater than 110% of level T1, and/or the threshold amount may be a tolerable fraction of a different between level T2 and level T1. In some embodiments, torque level T2 may be in excess of torque level T1 as a result of an operational stress on member 102, or an inadvertent over-tightening or galling of member 102 during maintenance thereof. In such a case, among others, the operator may identify that member 102 is over-tightened (or has been over-tightened) by operating inspection device 106. For example, the operator may operate inspection device 106 to emit radiation R2 toward sensor 108. Sensor 108 may absorb radiation R2. In response to absorption of radiation R2, sensor 108 may emit signal S2. Detector 110 may receive signal S2. Inspection device 106 may determine one or more of torque level T2 and force level F2 based at least in part on reception of signal S2 by detector 110. For example, circuitry 114 may be configured to determine one or more of torque level T2 and force level F2 by comparing signal S2 (e.g., spectral information associated therewith) against a standard, such as respective spectral information associated with one or more of radiation R2 and signal S5. Further, based at least in part on the determination by circuitry 114 of one more of torque level T2 and force level F2, circuitry 114 may emit a third user signal to the operator indicating that the torque applied to first member 102 (e.g., relative to second member 104) has exceeded the predetermined appropriate (and/or desirable) application of torque (e.g., torque level T1) for fastening together members 102, 104 by at least the threshold amount of torque (e.g., as described above).

Accordingly, in response to reception of the third user signal, the operator may reverse at least a portion of the torque applied to first member 102 relative to second member 104. For example, the operator may "loosen" first member 102 relative to second member 104 until the torque on first member 102 relative to second member 104 returns to torque level T1. In some embodiments, the operator reversing at least a portion of the torque may involve the operator disengaging members 102, 104, and/or replacing member 102 with another member. For example, torque level T3 may correspond to a damaged state of member 102, and as such, emission of signal S3 may indicate to the operator (e.g., via inspection device 106) that member 102 is no longer suitable for being fastened to or with second member 104.

While monitoring/testing of one member (e.g., member 102) via emission of photo-luminescent signals from one sensor (e.g., sensor 108) included in that one member is shown in FIGS. 1-4 and described above, inspection device 106 (or a similar system) may be used to concurrently monitor/test a plurality of members each having a sensor (e.g., similar to sensor 108). Further, monitoring/testing may be performed without an inspection device. For example, sensor(s) included in the members may be configured to emit visual photo-luminescent signals. For example, fluorophores in respective polymer layers of the respective sensor(s) may be configured to emit signals S1, S2, S3 in a spectrum of light that is visible to an unaided human eye in response to absorption of UV light, which may or may not be directed toward the sensor(s) by the operator.

In some embodiments, signals S1-S5 may correspond to color change signals. For example, radiation R1, R2, R3, R4, R5 may correspond to respective photons characterized by a first wavelength, and signals S1, S2, S3, S4, S5 may correspond to respective characterizing wavelengths of photon(s) emitted from sensor 108 that are shifted as compared to the first wavelength. For example, the characterizing wavelength of signal S5 may be shifted relative to the first wavelength by a first amount for producing a first color change indicative of the baseline internal torque of first member 102. The characterizing wavelength of signal S3 may be shifted relative to the first wavelength by a second amount for producing a second color change indicative of one or more of force level F3 and torque level T3. The characterizing wavelength of signal S1 may be shifted relative to the first wavelength by a third amount for producing a third color change indicative of one or more of force level F1 and torque level T1. The characterizing wavelength of signal S2 may be shifted relative to the first wavelength by a fourth amount for producing a fourth color change indicative of one or more of force level F2 and torque level T2. In some embodiments, one or more of the color changes may be in a non-visible spectrum. For example, one or more of the characterizing wavelengths of signals S1-S5 may correspond to a UV or an IR portion of the electromagnetic spectrum.

In some embodiments, signals S1-S5 may correspond to polarization signals. For example, signals S1-S5 may correspond to different characterizing polarizations of anisotropic light emitted from sensor 108 in response to absorption of respective radiation R1-R5.

In some embodiments, signals S1-S5 may correspond to lifetime signals. For example, signals S1-S5 may each correspond to a different duration of time between absorption of respective radiation R1-R5 by sensor 108 and emission of a photon in response to absorption of respective radiation R1-R5.

In some embodiments, one or more of signals S1-S5 may include a combination of a color change signal, a polarization signal, and/or a lifetime signal.

Example 2

This example describes a system 500 including a first member 502, a second member 504, and a tool 506; see FIGS. 5-7.

System 500 is an embodiment of system 100. For example, first member 502 may be configured for forceful engagement with second member 504, and may include a sensor 508 configured to emit one or more photo-luminescent signals indicative of the forceful engagement of first member 502 with second member 504. Further, tool 506 may include an inspection device 509 (see FIG. 6), which may comprise a detector 510, an emitter 512, and circuitry 514. Detector 510 may be configured to system 500 in a manner similar to detector 110 in system 100. Similarly, emitter 512 and circuitry 514 may be configured to system 500 in a manner similar to emitter 112 and circuitry 114 in system 100, respectively. For example, detector 510 may be configured to receive the one or more photo-luminescent signals, which may be emitted from sensor 508 in response to absorption of radiation from emitter 512. Circuitry 514 may be configured to determine the level of force (and/or torque) associated with the forceful engagement of members 502, 504, based at least in part on reception of the one or more photo-luminescent signals by detector 510, for example, by comparing spectral information associated therewith against a standard.

In particular, as shown in FIG. 5, first member 502 is a bolt including a threaded shaft (or shaft portion) 520, and a head (or head portion) 522. Portions 520, 522 may be connected to one another. For example, shaft portion 520 may be fixedly attached, integral with, and/or extend from head portion 522.

Threaded shaft 520 may include an internal channel 524. As shown, internal channel 524 has a surface 524a that is coated with (at least a portion of) sensor 508. For example, sensor 508 may include fluorescent dye (or fluorescent dye molecules) 530 embedded in at least one layer of polymer 532 or other deformable material (see FIG. 6). Similar to the fluorescent dye described above, dye 530 may have a property that changes as a function of force applied to first member 502 for emission of the one or more photo-luminescent signals (e.g., with differing signals being emitted at different force or torque levels). More specifically, induced fluorescence (e.g., by the inspection device) of molecules 530 may change with deformation of polymer 532 (e.g., resulting from forces on first member 502). As the local environment of the fluorescent dye molecules 530 is deformed, the proximity of molecules 530 to one another may be changed, either increased or decreased depending on, for example, the molecular mobility of molecules 530 in polymer 532. The probability of molecules 530 to form aggregates may then also be changed, and as a result the fluorescent behavior (or properties) of molecules 530 may be changed as well.

For example, molecules 530 with intrinsic dipole moments may be selected and incorporated into polymer 532. When stress is applied to polymer 532 (e.g., via force and/or torque applied to first member 502 by one or more of tool 506 and second member 504), positions of molecules 530 may shift as a network of polymer 532 displaces. This shift may change the aggregation behavior of molecules 530, and therefore may also change their fluorescent property (or behavior) as a result, for example in a manner similar to the changing fluorescent behavior of the fluorescent dye molecules disclosed in U.S. Pat. No. 8,720,278.

For example, molecules 530 may be based on a modified stilbene-type fluorescent molecule customized with differing end groups designed to control their solubility and interaction with polymer 530. The modified stilbene-type fluorescent molecule may exhibit a large amount of conjugation that may allow its electron density to move both within the molecule, for monomer-type excitation, and out-of-plane when in proximity with another stilbene, for dimer excitation.

In some embodiments, the inspection device of tool 506 may include (or be) a photo-luminescent device, similar to device 618 disclosed in U.S. Pat. No. 8,720,278. For example, the photo-luminescent device of tool 506 may be used to collect photo-luminescent quantum yield (PLQY) and fluorescence emission spectra. For example, emitter 512 may be included in the photo-luminescent device of tool 506 and may emit EM radiation R6, and identify a fluorescence emission (or photo-luminescent signal) S6 from molecules 530 within polymer 532. Fluorescence emission S6, among other photo-luminescent signals emitted from sensor 508, may be stored as a fluorescence profile within circuitry 514, and accessed for monitoring/testing the fastening of first member 502 with second member 504, as will be described further below in continuing detail.

Referring back to FIG. 5, as mentioned above, at least a portion of sensor 508 may be coated on surface 524a. As also shown in FIG. 5, surface 524a may be a generally conical surface (e.g., a frusto-conical surface, and/or a surface having opposing faces that taper toward one another). Further, the generally conical surface may be tapered along a length of threaded shaft 520. Such a configuration of sensor 508 coated on generally conical surface 524a may permit different photo-luminescent signals to be received from different portions of sensor 508 in proximity to different portions of threaded shaft 520, as will also be described further below in more detail.

In some embodiments, an optically transmissive core 536 may be disposed in channel 524. Core 536 may be made of a generally optically transparent polyethylene terephthalate (PET), or any other suitable material configured to permit transit of the one or more photo-luminescent signals from sensor 508 through core 536 and out of an opening 524b of channel 524 in head 522.

Core 536 may be disposed in channel 524, such that sensor 508 is sandwiched between an outer surface 536a of core 536 and surface 524a of channel 524. As shown, core 536 may be similarly generally conical in shape so as to compliment surface 524a. In some embodiments, core 536 may fill a majority of a volume (e.g., an overall volume) of channel 524, and/or may be secured, fixed, attached, and/or coupled to surface 524a (e.g., via polymer layer 532), which may reinforce threaded shaft 520 and/or improve transmission of torque from head 522 to shaft 520.

In particular, as shown in FIG. 5, the length of threaded shaft 520 may extend along an axis A1. Axis A1 may correspond to a rotational axis of first member 502 about which torque may be applied to engage threads of threaded shaft 520 with second member 504. The threads (or thread) of threaded shaft 520 may helically extend from threaded shaft 520 about axis A1.

As shown, second member 504 may be an object, such as a base or a nut, having an aperture 540 for receiving threaded shaft 520. In particular aperture 540 may have a threaded surface, which may be generally complimentary to an external surface of threaded shaft 520, and with which the threads of threaded shaft 520 may be forcefully engaged via torque applied to head 522 and transmitted to threaded shaft 520.

In an exemplary operation of system 500, shaft 520 may be extended through an aperture 550 in a third member 552, and then engaged with aperture 540 in second member 504. Tool 506 may be used (or operated) to apply torque to threaded shaft 520 relative to second member 504 and thereby draw head 522 and second member 504 toward one another (e.g., via the forceful engagement of the threads of threaded shaft 520 and the corresponding threads of aperture 540). In some embodiments, head 522 and second member 504 being drawn toward one another may involve only one of those components moving relative to the other. Further, head 522 and second member 504 being drawn toward one another may clamp third member 522 therebetween, as is shown in FIG. 6.

In particular, tool 506 may include a tightening device 560 configured to apply force to first member 502 engaged with second member 504. In particular, tightening device 560 may include a torque generator 562, a socket 564, and a torque transmission-control mechanism 566. For example, torque generator 562 may include a handle (e.g., a wrench handle) or other suitable device, mechanism, apparatus, or structure, and/or combination thereof (e.g., an electrically powered driver, such as that of an impact wrench) for generating a torque about axis A1. Socket 564 may be configured to receive and torque head portion 522 (e.g., about axis A1 and relative to second member 504) via torque generated by torque generator 562. In some embodiments, torque generated by torque generator 562 may be transmitted to socket 564 via mechanism 566.

Further, inspection device 509 may be coupled to tightening device 560. As mentioned above, inspection device 509 may be configured to receive a photo-luminescent signal, such as signal S6, emitted from first member 502, wherein the photo-luminescent signal indicates a level of force (e.g., a level of torque, or a torque level) applied to first member 502 by tightening device 560. For example, emitter 512 may be configured to emit EM radiation, such as radiation R6, toward sensor 508. Sensor 508 may be configured to emit the photo-luminescent signal, such as signal S6, in response to absorption of the EM radiation from emitter 512. Inspection device 509 may be configured to receive the photo-luminescent signal from sensor 508 via socket 564. For example, detector 510 may be configured to receive signal S6 from sensor 508 through socket 564 (e.g., through a recess defined by socket 564 for receiving and torqueing head portion 522).

In some embodiments, inspection device 509 may be configured to prevent tightening device 560 from further substantially forcefully engaging first member 502 with (and/or relative to) second member 504 based at least in part on reception of photo-luminescent signal S6 (or another photo-luminescent signal emitted from sensor 508). For example, circuitry 514 may be configured to receive (or acquire) signal S6 (or spectral information associated therewith) from detector 510. Circuitry 514 may be configured to determine a torque level on first member 502 based at least in part on signal S6. For example, circuitry 514 may be configured to compare spectral information associated with signal S6 to a standard (e.g., spectral information associated with radiation R6, or a previously acquired baseline signal from sensor 508). If circuitry 514 determines that first member 502 has not yet been torqued to a predetermined appropriate torque level, then circuitry 514 may operate mechanism 566 to permit torque to be transmitted from generator 562 to socket 564 for further forcefully torqueing head portion 522 relative to second member 504 about axis A1. However, if circuitry 514 determines that first member 502 has reached the predetermined torque level, then circuitry 514 may operate mechanism 566 to prevent torque from being transmitted from generator 562 to socket 564 thereby preventing further torqueing of first member 502 relative to second member 504 about axis A1.

In some embodiments, inspection device 509 may be configured to provide a signal to a user that indicates a level of force applied to the first member. For example, circuitry 514 may be configured to provide one or more of an audible signal, a visual signal, and a haptic signal to the user that is indicative of the determined force level. In some embodiments, circuitry 514 may be configured to both operate mechanism 566 to prevent and/or permit transmission of torque to socket 564 based on signal S6, and provide corresponding audible, visual, and/or haptic signals to the user.

More specifically, the user may operate tightening device 560 to torque first member 502 about axis A1 (and relative to second member 504) with a torque level T6. As the user is torqueing first member 502, emitter 512 may illuminate sensor 508 with radiation R6. In response to absorption of radiation R6, different portions of sensor 508 (e.g., corresponding to different vertical portions of threaded member 520 in FIG. 6) may emit different photo-luminescent signals. In particular, a distal portion 508a of sensor 508 may emit a photo-luminescent signal S7, a central portion 508b of sensor 508 may emit a photo-luminescent signal S8, and a proximal portion 508c of sensor 508 may emit a photo-luminescent signal S9, as can be seen in FIGS. 6 and 7. Signals S7, S8, S9 may travel through core 536 and socket 564 and be received by detector 510. In some embodiments, signal S6 may comprise signals S7, S8, S9.

Circuitry 514 may receive signals S7, S8, S9 from detector 510. Circuitry may determine (and/or approximate) respective force levels between respective portions 522a, 522b, 522c of threaded shaft 522 with corresponding respective portions 540a, 540b, 540c of threaded aperture 540. For example, signal S7 may indicate that a forceful engagement (e.g., a frictional engagement) between portions 520a, 540a corresponds to the predetermined appropriate torque level for fastening together members 502, 504. Signal S8 may indicate that a forceful engagement between portions 520b, 540b corresponds to a torque level below (e.g., less in magnitude than) the predetermined appropriate torque level for fastening together members 502, 504. Similarly, signal S9 may indicate that a forceful engagement between portions 520c, 540c corresponds to a torque level that is even less in magnitude that the predetermined appropriate torque level for fastening together members 502, 504. As depicted, the generally conical shape of surface 524a upon which sensor 508 is coated may permit these signals to be received from various depths within threaded shaft 520 along axis A1, which may permit more precise monitoring and/or testing of the forceful engagement between members 502, 504, for example, to determine whether first member 502 is properly seated in second member 504.

For example, in one embodiment, a user may enter various parameters associated with one or more of members 502, 504 (and/or 552) into circuitry 514 (e.g., by loading a program onto memory therein). Circuitry 514 may operate mechanism 566 (and/or generator 562 in some embodiments) to permit appropriate torque to be applied to head portion 522, so that the desired forceful engagement between one or more of the portions of threaded shaft 522 and one or more portions of threaded aperture 540 may be achieved. For example, if in the particular application it is desirable for none of portions 540a, 540b, 540c to be overly forcefully engaged with threaded aperture 540, then reception of signal S7 and the determination of the associated torque level by circuitry 514 may be used to operate mechanism 566 to prevent further torque from being applied to head 522 (e.g., in the same direction as torque level T6), and/or may be used to emit a signal to the user indicating that the torque level on portion 520a has reached the predetermined appropriate torque level, but that torque levels on portions 520b, 520c have not reached the predetermined appropriate torque level.

However, in other applications, various combinations may be achieved. For example, it may be desirable for a majority (or other suitable percentage) of the length of threaded member 520 to be torqued to the predetermined appropriate torque level, and for an average of torque levels along the entire length to not exceed the predetermined appropriate torque level. In which case, based on signals S7, S8, S9, circuitry 514 may operate mechanism 566 to permit further application of torque, and/or otherwise signal the user to indicate that further application of torque is desirable. If the average of the torque levels of threaded member 520 along its length reaches the predetermined appropriate torque level, but the majority (or other suitable percentage) of the length has not reached the predetermined appropriate torque level, then circuitry 514 may operate mechanism 566 to prevent further application of torque to head portion 522 (e.g., in the direction of torque level T6), and/or may signal to the user that members 502, 504 are currently not suitable for being fastened together (and/or that corrective action may be appropriate, such as removing first member 502 from second member 504, and/or inspecting one or more of members 502, 504). However, if the average torque level of the majority (or other suitable percentage) of the length of threaded member 522 reaches the predetermined appropriate torque level, then circuitry 514 may operate mechanism 566 to prevent further application of torque to head portion 520 and/or may emit a corresponding signal to the user.

In FIG. 7, signals S7, S8, S9 are depicted as different color changes (e.g., with different shading densities corresponding to different characterizing wavelengths of the respective signals) of respective sensor portions 508a, 508b, 508c, however, in other embodiments, one or more of these signals may correspond to polarization changes, lifetime changes, or other suitable photo-luminescent changes, such as varying levels of quenching or photo-emission intensity. Further, while signals S7, S8, S9 are described above as indicating respective torque levels that decrease in magnitude, it should be appreciated that in other examples and particular applications more or less signals may be concurrently emitted from different portions of sensor 508, and/or may indicate other corresponding torque levels.

Further, while one layer of polymer 532 with embedded molecules 530 is depicted as being included in sensor 508, in other embodiments, sensor 508 may comprise two or more layers of different polymers having different network characteristics (e.g., hardnesses), and/or two or more different molecules having different photo-luminescent properties in different layers. These different layers, which may have different photo-luminescing molecules, may be co-axial with and/or in contact with depicted layer 532. As such, the differing displacements of these layers from surface 524a (and/or from the outer surface of threaded shaft 520, and/or differing associated or proximal thicknesses of threaded shaft 520) may be configured to provide photo-luminescent at and indicative of different torque levels.

Moreover, while sensor 508 has been described as including molecules 530, which may dimerize when polymer 532 is put under stress, in other embodiments, surface 524a may be etched, and a first encapsulated chemical reactant, such as ozone (NO), may be disposed therein. An outer surface 532a of polymer (or another deformable material) 532 may be coated with a second encapsulated chemical reactant, such as nitric oxide ($O_3$), and forceful engagement between threaded aperture 540 and threaded shaft 520 may cause the first and second encapsulated reactants to come into proximity with one another and combine to form a chemiluminescent composition, which may comprise sensor 508 in the form of a sensor material. In other embodiments, the first and second encapsulated reactants may combine to form a photo-luminescent sensor material described further above in conjunction with U.S. Patent Application No. 20080204752, with the sensor material being configured to emit one or more luminescent (e.g., photo-luminescent) signals described herein. In such an embodiment, layer 532 may be included in core 536. The encapsulation may include multiple encapsulation compositions resulting in luminescence to indicate proper torque (or other force level) at green (or another first color), insufficient torque at yellow (or another second color), and over-torque at red (or another third color). As such, respective applications of proper torque, insufficient torque, and over-torque may result in sensor 508 luminescing (e.g., "glowing") at three respectively distinct colors.

Example 3

This example describes a system 800 including a first member 802 (e.g., a washer), a second member 804 (e.g., a bolt), a third member 806, and a tool 808; see FIGS. 5-7.

System 800 is an embodiment of system 100. For example, first member 802 may be configured for forceful engagement with second member 804 (and third member 806), and may include a sensor 810 configured to emit one or more photo-luminescent signals indicative of the forceful engagement of first member 802 with second member 804 (e.g., a forceful engagement of first member 802 between members 804, 806). Further, tool 808 may include an inspection device 812 (see FIG. 9), which may comprise a detector 814, an emitter 816, and circuitry 818. Detector 814 may be configured to system 800 in a manner similar to detector 110 in system 100 and/or in a manner similar to detector 510 in system 500. Similarly, emitter 816 and circuitry 818 may be configured to system 800 in a manner similar to emitter 112 and circuitry 114 in system 100, respectively, and/or in a manner similar to emitter 512 and circuitry 514 in system 500, respectively. For example, detector 814 may be configured to receive the one or more photo-luminescent signals from sensor 810, which may be emitted from sensor 810 in response to absorption of EM radiation from emitter 816. Circuitry 818 may be configured to determine the level of force (and/or torque) associated with the forceful engagement of member 802 between (and/or with) members 804, 806 based at least in part on reception of the one or more photo-luminescent signals by detector 814, for example, by comparing spectral information associated therewith against a standard.

In particular, as shown in FIG. 8, second member 804 may be a bolt having a threaded shaft 820 similar to threaded shaft 520, and a head portion 822 similar to head portion 522. Third member 806 may be an object having a threaded aperture 824 (e.g., similar to member 504 having threaded aperture 540) for receiving and being forcefully engaged with threaded shaft 820.

As also shown in FIG. 8, washer 802 may include a structural member 830. Member 830 may be made of metal, plastic, or other suitable washer material. Member 830 may have first and second opposing surfaces 830a, 830b through which a central aperture 834 may be defined for receiving shaft 820 (or other suitable fastening member). Sensor 810 may be similar to sensor 508 (e.g., may include a layer of polymer or other deformable material, and may be embedded with fluorescent dye molecules that have a photo-luminescent property that changes as a function of force applied to the layer of polymer or other suitable deformable material). Sensor 810 may be coated on one or more of surfaces 830a, 830b. As shown, sensor 810 is coated on surface 830b. Sensor 810 may be configured to emit one or more photo-luminescent signals, as mentioned above, such as signal S10, indicative of one or more levels of force transmitted to structural member 830 through which shaft 820 extends opposite head portion 822 relative to structural member 830, as shown in FIG. 9.

For example, in an exemplary operation of system 800, shaft 820 may be extended through aperture 834, and then engaged with aperture 824. Tool 806 may be used (or operated) to apply torque to threaded shaft 820 relative to member 806 and thereby draw head 822 and member 806 toward one another (e.g., via the forceful engagement of the threads of threaded shaft 820 and corresponding threads of aperture 824). In some embodiments, head 822 and member 806 being drawn toward one another may involve only one of those components moving relative to the other. Further, head 822 and member 806 being drawn toward one another may clamp washer 802 therebetween, as is shown in FIG. 9.

In particular, tool 808 may include a tightening device 860 (e.g., similar to tightening device 560) configured to apply force to member 804. In particular, tightening device 860 may include a torque generator 862 (e.g., similar to generator 562), a socket 864 (e.g., similar to socket 564), and a torque transmission-control mechanism 866 (e.g., similar to mechanism 566). For example, generator 862 may be configured for generation of torque about axis A2 (e.g., associated with a long axis of shaft 820 in a similar fashion as axis A1 may be with shaft 520). Socket 864 may be configured to receive and torque head portion 822 (e.g., about axis A2 and relative to member 806) via torque generated by torque generator 862. In some embodiments, torque generated by torque generator 862 may be transmitted to socket 864 via mechanism 866, in a manner similar to that of mechanism 566. For example, inspection device 812 may be coupled to tightening device 860, in a manner similar to that of the coupling between devices 509, 512, such that mechanism 866 may be operated by circuitry 818 to prevent and/or permit transmission of torque to socket 864 based on one or more of the photo-luminescent signals from sensor 810.

More specifically, tightening device may be configured to apply a torque T10 to head 822 about axis A2 relative to member 806 (e.g., via torque generated by generator 862 and transmitted to socket 864). Torque T10 may forcefully engage threaded shaft 820 with a corresponding threaded surface 824a of aperture 824, thereby drawing head 822 toward member 806 and clamping washer 802 therebetween. For example, clamping washer 802 may involve members 804, 806 exerting a compressive force to (and/or on) washer 802, which may be associated with torque T10.

While (and/or after) tightening device 808 is applying torque T10 to head 822, emitter 816 may emit EM radiation R10 toward sensor 810. In response to absorption of radiation R10, sensor 810 may emit signal S10, which may be received by detector 814. Signal S10 may be indicative of at least a first predetermined level of force applied to washer 802 (e.g., to structural member 830 via sensor 810 and/or between members 804, 806). For example, the first predetermined level of force may be associated with a predetermined appropriate level of forceful engagement between members 804, 806 (e.g., between their respective threads). For example, signal S10 may correspond with signal S1 (see FIG. 1). In some embodiments, the first predetermined level of force applied to washer 802 may correspond to a force level that exceeds the predetermined appropriate level of forceful engagement by at least a threshold amount (e.g., the first predetermined level of force may correspond to 110%, or other excessive percentage, of the predetermined appropriate level, with the threshold amount corresponding to a difference between the first predetermined level of force and the predetermined appropriate level, which in a non-limiting example may be about 1 N of force). In such a case, signal S10 may correspond to signal S2 (see FIG. 1). In some embodiments, the first predetermined level of force applied to washer 802 may correspond to a force level that is less than the predetermined appropriate level of forceful engagement, in which case signal S10 may correspond to signal S3 (see FIG. 1).

For example, if signal S10 corresponds with signal S1, then inspection device 812 may operate mechanism 866 to prevent further torque from being applied to head 822, and/or may emit a user signal to an operator of tool 808 indicating that appropriate forceful engagement between members 804, 806 has been reached.

Further, if signal S10 corresponds with signal S2, then inspection device 812 may operate mechanism 866 to prevent further torque from being applied to head 822, and/or may emit a user signal to an operator of tool 808 indicating that appropriate forceful engagement between members 804, 806 has been exceeded (and/or that corrective action may be desirable).

Moreover, if signal S10 corresponds with signal S3, then inspection device 812 may operate mechanism 866 to permit further torque to be applied to head 822, and/or may emit a user signal to an operator of tool 808 indicating that appropriate forceful engagement between members 804, 806 has not yet been reached.

As depicted in FIG. 9, detector 814 may be configured to receive signal S10 through socket 864, and emitter 816 may be configured to emit radiation R10 to sensor 810 through socket 864, in a manner similar to that depicted in system 500, but here in system 800, the detector and emitter respectively receive and emit via a skirt portion of socket 864 adjacent head 822 rather than via a central portion of the socket "above" the head.

Further, in some embodiments, a sensor 900 (depicted here with dash double dot lines) may be coated on a surface of head 822 that contacts washer 802 (or member 806 if washer 802 is not included) when shaft 820 is engaged with member 806 (and/or with washer 802 if washer 802 is included). Sensor 900 may be configured to emit one or more photo-luminescent signals (e.g., similar to sensor 810) for indicating one or more associated torque and/or force levels, in a similar fashion. For example, the one or more photo-luminescent signals emitted from sensor 900 may be received by detector 814, and/or may be emitted in response to absorption of EM radiation from emitter 816.

Similarly, in some embodiments, a surface of member 806 may be coated with a sensor 950 (e.g., similar to sensor 810), which is also shown in dash double dot lines in FIG. 9. Sensor 950 may be configured to produce one or more photo-luminescent signals (e.g., via absorption of EM radiation from emitter 816), which may be received by detector 814 for determination of the associated force level by inspection device 812 and/or operation of tightening device 808.

Accordingly, head portion 822 may have a surface (e.g., a lower surface in FIG. 9) that may contact a surface of member 806 (e.g., an upper surface of member 806 in FIG. 9) when shaft portion 820 is engaged with member 806 (e.g., if washer 802 is not included). Further, one or more of the surface of head portion 822 and the surface of member 806 that contact one another (e.g., if washer 802 is not included) may be coated with at least a portion of a sensor (e.g., sensor 900 or sensor 950, or each of sensors 900, 950 including different reactants) that when combined together form a sensor material), wherein the sensor is configured to emit a first photo-luminescent signal to a detector when at least a predetermined first torque level is applied to head 822 when members 804, 806 are engaged. For example, one or more compressive forces between these contacting surfaces may be indexed with one or more predetermined torque levels and thereby may be used to indicate the same.

Example 4

Figure 10:
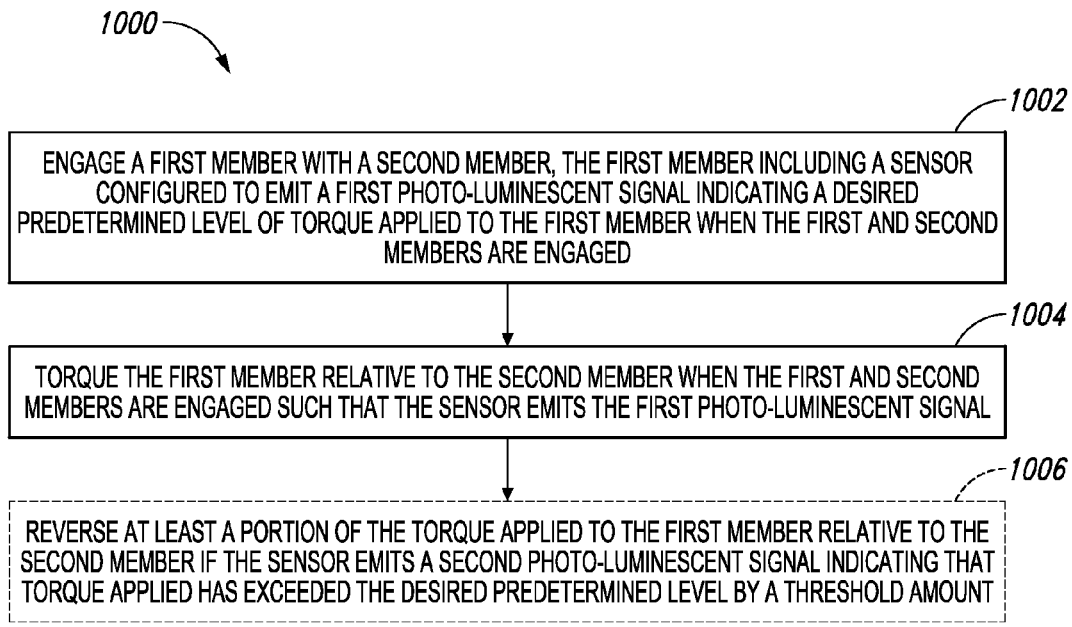
FIG. 10 is a flowchart depicting a method.

This example describes a method, which may be used to torque a fastener; see FIG. 10.

FIG. 10 is a flowchart illustrating steps performed in an illustrative method, and may not recite the complete process. FIG. 10 depicts multiple steps of a method, generally indicated at 1000, which may be performed in conjunction with one or more components, functionalities, and/or steps of the examples described herein. Although various steps of method 1000 are described below and depicted in FIG. 10, the steps need not necessarily all be performed, and in some cases may be performed in a different order than the order shown.

As shown, method 1000 may include a step 1002 of engaging a first member with a second member. The first member may include a sensor configured to emit a first photo-luminescent signal indicating a desired predetermined level of torque applied to the first member when the first and second members are engaged. For example, the first photo-luminescent signal may correspond to signal S1 (see FIG. 4).

As also shown in FIG. 10, method 1000 may further include a step 1004 of torqueing the first member relative to the second member when the first and second members are engaged such that the sensor emits the first photo-luminescent signal.

In some embodiments, the sensor may be configured to emit a second photo-luminescent signal. The second photo-luminescent signal may indicate that torque applied to the first member is below the desired predetermined level. In such embodiments, torqueing the first member relative to the second member may involve torqueing the first member until the sensor ceases to emit the second photo-luminescent signal.

In some embodiments, the sensor may be configured to emit a third photo-luminescent signal. The third photo-luminescent signal may indicate that torque applied to the first member has exceeded the desired predetermined level by (at least) a threshold amount (e.g., the torque applied may in some embodiments correspond to 110%, or other excessive percentage, of the desired predetermined level, and the threshold amount may correspond to a difference between the desired predetermined level and 110% of the desired predetermined level, or fraction thereof). In some embodiments, method 1000 may further include a step 1006 of reversing at least a portion of the torque applied to the first member relative to the second member if the sensor emits the third photo-luminescent signal. In some embodiments, step 1006 may involve disengaging the first and second members.

Example 5

Figure 11:
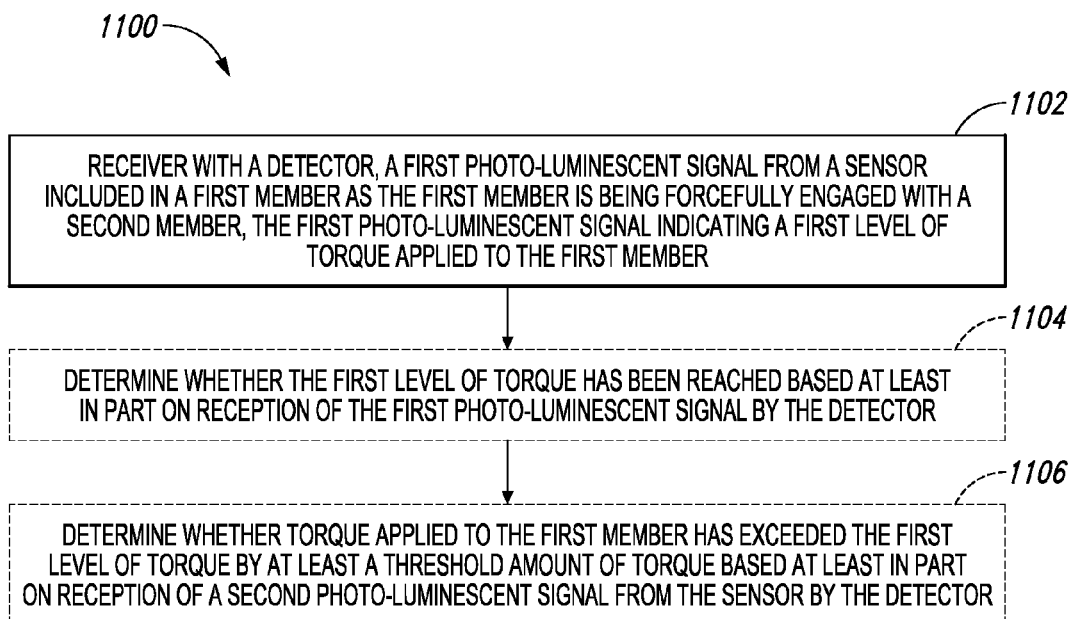
FIG. 11 is a flowchart depicting another method.

This example describes a method, which may be used to determine torque applied to a fastener; see FIG. 11.

FIG. 11 is a flowchart illustrating steps performed in an illustrative method, and may not recite the complete process. FIG. 11 depicts multiple steps of a method, generally indicated at 1100, which may be performed in conjunction with one or more components, functionalities, and/or steps of the examples described herein. Although various steps of method 1100 are described below and depicted in FIG. 11, the steps need not necessarily all be performed, and in some cases may be performed in a different order than the order shown.

As shown, method 1100 may include a step 1102 of receiving with a detector, a first photo-luminescent signal from a sensor included in a first member. For example, at step 1102, the first photo-luminescent signal may be received by the detector as the first member is being forcefully engaged with a second member. The first photo-luminescent signal may indicate a first level of torque applied to the first member, which may be associated with the forceful engagement of the first member with the second member. In some embodiments, the detector may be (or include) an electronic photo-detector included in an inspection system. Further, in some embodiments, step 1102 may be preceded by a step of directing ultraviolet light toward the sensor from an illuminator, which may be included in the inspection system. For example, the sensor may be configured to emit the first photo-luminescent signal in response to absorption of the ultraviolet light from the illuminator.

In some embodiments, method 1100 may further include a step 1104 of determining with the inspection system whether the first level of torque has been reached based at least in part on reception of the first photo-luminescent signal by the electronic photo-detector.

In some embodiments, the first level of torque may correspond with a desired level of torque for forceful engagement of the first member with the second member. The sensor may be further configured to emit a second photo-luminescent signal indicating that torque applied to the first member has exceeded the first level by at least a threshold amount of torque. In such embodiments, among others, method 1100 may further include a step 1106 of determining whether torque applied to the first member has exceeded the first level by at least the threshold amount of torque based at least in part on reception of the second photo-luminescent signal by the detector (e.g., by the electronic photo-detector).

Example 6

This example describes a data processing system 1200 in accordance with aspects of the present disclosure. In this example, data processing system 1200 is an illustrative data processing system for implementing circuitry 114, 514, and 818 in FIGS. 1-4, 6, and 9; See FIG. 12.

In this illustrative example, data processing system 1200 includes communications framework 1202. Communications framework 1202 provides communications between processor unit 1204, memory 1206, persistent storage 1208, communications unit 1210, input/output (I/O) unit 1212, and display 1214. Memory 1206, persistent storage 1208, communications unit 1210, input/output (I/O) unit 1212, and display 1214 are examples of resources accessible by processor unit 1204 via communications framework 1202.

Processor unit 1204 serves to run instructions that may be loaded into memory 1206, such as one or more instructions related to one or more parameters (e.g., characteristics or properties) of one or more of the members disclosed herein. Processor unit 1204 may be a number of processors, a multi-processor core, or some other type of processor, depending on the particular implementation. Further, processor unit 1204 may be implemented using a number of heterogeneous processor systems in which a main processor is present with secondary processors on a single chip. As another illustrative example, processor unit 1204 may be a symmetric multi-processor system containing multiple processors of the same type.

Memory 1206 and persistent storage 1208 are examples of storage devices 1216. A storage device is any piece of hardware that is capable of storing information, such as, for example, without limitation, data, program code in functional form, and other suitable information either on a temporary basis or a permanent basis.

Storage devices 1216 also may be referred to as computer readable storage devices in these examples. Memory 1206, in these examples, may be, for example, a random access memory or any other suitable volatile or non-volatile storage device. Persistent storage 1208 may take various forms, depending on the particular implementation.

For example, persistent storage 1208 may contain one or more components or devices. For example, persistent storage 1208 may be a hard drive, a flash memory, a rewritable optical disk, a rewritable magnetic tape, or some combination of the above. The media used by persistent storage 1208 also may be removable. For example, a removable hard drive may be used for persistent storage 1208.

Communications unit 1210, in these examples, provides for communications with other data processing systems or devices. In these examples, communications unit 1210 is a network interface card. Communications unit 1210 may provide communications through the use of either or both physical and wireless communications links.

Input/output (I/O) unit 1212 allows for input and output of data with other devices that may be connected to data processing system 1200. For example, input/output (I/O) unit 1212 may provide a connection for user input through a keyboard, a mouse, and/or some other suitable input device. Further, input/output (I/O) unit 1212 may send output to a printer. Display 1214 provides a mechanism to display information to a user.

Instructions for the operating system, applications, and/or programs may be located in storage devices 1216, which are in communication with processor unit 1204 through communications framework 1202. In these illustrative examples, the instructions are in a functional form on persistent storage

1208. These instructions may be loaded into memory 1206 for execution by processor unit 1204. The processes of the different embodiments may be performed by processor unit 1204 using computer-implemented instructions, which may be located in a memory, such as memory 1206.

These instructions are referred to as program instructions, program code, computer usable program code, or computer readable program code that may be read and executed by a processor in processor unit 1204. The program code in the different embodiments may be embodied on different physical or computer readable storage media, such as memory 1206 or persistent storage 1208.

Program code 1218 is located in a functional form on computer readable media 1220 that is selectively removable and may be loaded onto or transferred to data processing system 1200 for execution by processor unit 1204. Program code 1218 and computer readable media 1220 form computer program product 1222 in these examples. In one example, computer readable media 1220 may be computer readable storage media 1224 or computer readable signal media 1226.

Computer readable storage media 1224 may include, for example, an optical or magnetic disk that is inserted or placed into a drive or other device that is part of persistent storage 1208 for transfer onto a storage device, such as a hard drive, that is part of persistent storage 1208. Computer readable storage media 1224 also may take the form of a persistent storage, such as a hard drive, a thumb drive, or a flash memory, that is connected to data processing system 1200. In some instances, computer readable storage media 1224 may not be removable from data processing system 1200.

In these examples, computer readable storage media 1224 is a physical or tangible storage device used to store program code 1218 rather than a medium that propagates or transmits program code 1218. Computer readable storage media 1224 is also referred to as a computer readable tangible storage device or a computer readable physical storage device. In other words, computer readable storage media 1224 is a media that can be touched by a person.

Alternatively, program code 1218 may be transferred to data processing system 1200 using computer readable signal media 1226. Computer readable signal media 1226 may be, for example, a propagated data signal containing program code 1218. For example, computer readable signal media 1226 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 1218 may be downloaded over a network to persistent storage 1208 from another device or data processing system through computer readable signal media 1226 for use within data processing system 1200. For instance, program code stored in a computer readable storage medium in a server data processing system may be downloaded over a network from the server to data processing system 1200. The data processing system providing program code 1218 may be a server computer, a client computer, or some other device capable of storing and transmitting program code 1218.

The different components illustrated for data processing system 1200 are not meant to provide architectural limitations to the manner in which different embodiments may be implemented. The different illustrative embodiments may be implemented in a data processing system including components in addition to and/or in place of those illustrated for data processing system 1200. Other components shown in FIG. 12 can be varied from the illustrative examples shown. The different embodiments may be implemented using any hardware device or system capable of running program code. As one example, data processing system 1200 may include organic components integrated with inorganic components and/or may be comprised entirely of organic components excluding a human being. For example, a storage device may be comprised of an organic semiconductor.

In another illustrative example, processor unit 1204 may take the form of a hardware unit that has circuits that are manufactured or configured for a particular use. This type of hardware may perform operations without needing program code to be loaded into a memory from a storage device to be configured to perform the operations.

For example, when processor unit 1204 takes the form of a hardware unit, processor unit 1204 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a field programmable logic array, a field programmable gate array, and other suitable hardware devices. With this type of implementation, program code 1218 may be omitted, because the processes for the different embodiments are implemented in a hardware unit.

In still another illustrative example, processor unit 1204 may be implemented using a combination of processors found in computers and hardware units. Processor unit 1204 may have a number of hardware units and a number of processors that are configured to run program code 1218. With this depicted example, some of the processes may be implemented in the number of hardware units, while other processes may be implemented in the number of processors.

In another example, a bus system may be used to implement communications framework 1202 and may be comprised of one or more buses, such as a system bus or an input/output bus. Of course, the bus system may be implemented using any suitable type of architecture that provides for a transfer of data between different components or devices attached to the bus system.

Additionally, communications unit 1210 may include a number of devices that transmit data, receive data, or both transmit and receive data. Communications unit 1210 may be, for example, a modem or a network adapter, two network adapters, or some combination thereof. Further, a memory may be, for example, memory 1206, or a cache, such as that found in an interface and memory controller hub that may be present in communications framework 1202.

The flowcharts and block diagrams described herein illustrate the architecture, functionality, and operation of possible implementations of systems, methods, and computer program products according to various illustrative embodiments. In this regard, each block in the flowcharts or block diagrams may represent a module, segment, or portion of code, which comprises one or more executable instructions for implementing the specified logical function or functions. It should also be noted that, in some alternative implementations, the functions noted in a block may occur out of the order noted in the drawings. For example, the functions of two blocks shown in succession may be executed substantially concurrently, or the functions of the blocks may sometimes be executed in the reverse order, depending upon the functionality involved.

Aspects of the present disclosure, such as torque determinations, etc., may be embodied as a computer method, computer system, or computer program product. Accordingly, aspects of the present disclosure may take the form of an entirely hardware embodiment, an entirely software embodiment (including firmware, resident software, microcode, and the like), or an embodiment combining software and hardware aspects, all of which may generally be referred to herein as a "circuit," "module," or "system." Furthermore, aspects of the present disclosure may take the form of a computer program product embodied in a computer-readable medium (or media) having computer readable program code/instructions embodied thereon.

Any combination of computer-readable media may be utilized. Computer-readable media can be a computer-readable signal medium and/or a computer-readable storage medium. A computer-readable storage medium may include an electronic, magnetic, optical, electromagnetic, infrared, and/or semiconductor system, apparatus, or device, or any suitable combination of these. More specific examples of a computer-readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, and/or any suitable combination of these and/or the like. In the context of this disclosure, a computer-readable storage medium may include any suitable tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, and/or any suitable combination thereof. A computer-readable signal medium may include any computer-readable medium that is not a computer-readable storage medium and that is capable of communicating, propagating, or transporting a program for use by or in connection with an instruction execution system, apparatus, or device.

Program code embodied on a computer-readable medium may be transmitted using any appropriate medium, including but not limited to wireless, wireline, optical fiber cable, RF, and/or the like, and/or any suitable combination of these.

Computer program code for carrying out operations for aspects of the present invention may be written in one or any combination of programming languages, including an object-oriented programming language such as Java, Smalltalk, C++, and/or the like, and conventional procedural programming languages, such as the C programming language. The program code may execute entirely on a user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), and/or the connection may be made to an external computer (for example, through the Internet using an Internet Service Provider).

Aspects of present embodiments are described above with reference to flowchart illustrations and/or block diagrams of methods, apparatuses, systems, and/or computer program products according to aspects of the present disclosure. Each block and/or combination of blocks in a flowchart and/or block diagram may be implemented by computer program instructions. The computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions can also be stored in a computer-readable medium that can direct a computer, other programmable data processing apparatus, and/or other device to function in a particular manner, such that the instructions stored in the computer-readable medium produce an article of manufacture including instructions which implement the function/act specified in the flowchart and/or block diagram block or blocks.

The computer program instructions can also be loaded onto a computer, other programmable data processing apparatus, and/or other device to cause a series of operational steps to be performed on the device to produce a computer-implemented process such that the instructions which execute on the computer or other programmable apparatus provide processes for implementing the functions/acts specified in the flowchart and/or block diagram block or blocks.

Any flowchart and/or block diagram in the drawings is intended to illustrate the architecture, functionality, and/or operation of possible implementations of systems, methods, and computer program products according to aspects of the present disclosure. In this regard, each block may represent a module, segment, or portion of code, which comprises one or more executable instructions for implementing the specified logical function(s). In some implementations, the functions noted in the block may occur out of the order noted in the drawings. For example, two blocks shown in succession may, in fact, be executed substantially concurrently, or the blocks may sometimes be executed in the reverse order, depending upon the functionality involved. Each block and/or combination of blocks may be implemented by special purpose hardware-based systems (or combinations of special purpose hardware and computer instructions) that perform the specified functions or acts.

Example 7

This section describes additional aspects and features of embodiments, presented without limitation as a series of paragraphs, some or all of which may be alphanumerically designated for clarity and efficiency. Each of these paragraphs can be combined with one or more other paragraphs, and/or with disclosure from elsewhere in this application, including the materials incorporated by reference, in any suitable manner. Some of the paragraphs below expressly refer to and further limit other paragraphs, providing without limitation examples of some of the suitable combinations.

A0. A fastening device comprising: a first member configured for forceful engagement with a second member, the first member including a sensor comprising a fluorescent dye embedded in a polymer, the fluorescent dye having a property that changes as a function of force applied to the first member for emission of a first photo-luminescent signal to a detector when at least a predetermined first torque level is applied to the first member when the first and second members are engaged; wherein the first photo-luminescent signal corresponds with a characterizing wavelength of a first photon emitted from the sensor in response to absorption of a second photon by the sensor, the characterizing wavelength of the first photon being shifted as compared to a characterizing wavelength of the second photon for producing a color change.

A1. The fastening device of paragraph A0, wherein the characterizing wavelength of the first photon corresponds to a wavelength of light that is non-visible to an unaided human eye.

A2. The fastening device of paragraph A0, wherein the sensor is configured to emit a second photo-luminescent signal indicating when a predetermined second torque level is applied to the first member when the first and second members are engaged.

A3. The fastening device of paragraph A2, wherein the first torque level corresponds to a predetermined appropriate application of torque to the first member for fastening the first and second members, and the second torque level corresponds to a predetermined inappropriate application of torque to the first member for fastening the first and second members.

A4. The fastening device of paragraph A3, wherein the second torque level is greater than the first torque level, the sensor being further configured to emit a third photo-luminescent signal indicating when a predetermined third torque level is applied to the first member when the first and second members are engaged, the third torque level being less than the first torque level.

A5. The fastening device of paragraph A0, wherein the first member includes a threaded shaft having an internal channel, the internal channel having a surface that is coated with at least a portion of the sensor.

A6. The fastening device of paragraph A5, wherein the surface that is coated with the sensor is a generally conical surface that is tapered along a length of the threaded shaft.

A7. The fastening device of paragraph A6, wherein an optically transmissive core is disposed in the internal channel such that the sensor is sandwiched between the core and the surface.

A8. The fastening device of paragraph A7, wherein the core fills a majority of a volume of the internal channel.

A9. The fastening device of paragraph A0, wherein the first member has a head portion and a shaft portion, the head portion having a surface that contacts a surface of the second member when the shaft portion is engaged with the second member, one or more of the surface of the head portion and the surface of the second member being coated with at least a portion of the sensor.

A10. The fastening device of paragraph A0, wherein the first member is a washer having a surface that is coated with the sensor, the washer contacting a surface of the second member when the washer and the second member are engaged.

A11. The fastening device of paragraph A0, wherein the second member is an object having an aperture for receiving the first member.

A12. The fastening device of paragraph A0, wherein the detector includes a human eye.

A13. The fastening device of paragraph A0, wherein the detector includes an electronic photo-detector configured to receive the first photo-luminescent signal, to generate a second signal based on and indicative of the first photo-luminescent signal, and to output the second signal to a user.

A14. The fastening device of paragraph A0, wherein the first torque level is at least 3 foot-pounds.

B0. A method comprising: engaging a first member with a second member, the first member including a sensor configured to emit a first photo-luminescent signal indicating a desired predetermined level of torque applied to the first member when the first and second members are engaged; and torqueing the first member relative to the second member when the first and second members are engaged such that the sensor emits the first photo-luminescent signal.

B1. The method of paragraph B0, wherein the sensor is configured to emit a second photo-luminescent signal indicating that torque applied to the first member has exceeded the predetermined level of torque by a threshold amount, the method further comprising reversing at least a portion of the torque applied to the first member relative to the second member if the sensor emits the second photo-luminescent signal.

B2. The method of paragraph B1, wherein reversing at least a portion of the torque applied involves disengaging the first and second members.

B3. The method of paragraph B0, wherein the sensor is configured to emit a second photo-luminescent signal indicating that torque applied to the first member is below the predetermined level, and torqueing the first member relative to the second member involves torqueing the first member until the sensor ceases to emit the second photo-luminescent signal.

C0. A method comprising: receiving with a detector, a first photo-luminescent signal from a sensor included in a first member as the first member is being forcefully engaged with a second member, the first photo-luminescent signal indicating a first level of torque applied to the first member that is associated with the forceful engagement of the first member with the second member.

C1. The method of paragraph C0, wherein the detector is an electronic photo-detector included in an inspection system, the method further comprising determining with the inspection system whether the first level of torque has been reached based at least in part on reception of the first photo-luminescent signal by the electronic photo-detector.

C2. The method of paragraph C1, further comprising directing ultraviolet light toward the sensor from an illuminator included in the inspection system, wherein the sensor is configured to emit the first photo-luminescent signal in response to absorption of the ultraviolet light.

C3. The method of paragraph C0, wherein the first level of torque corresponds with a desired level of torque for forceful engagement of the first member with the second member, the sensor being further configured to emit a second photo-luminescent signal indicating that torque applied to the first member has exceeded the first level by at least a threshold amount of torque, the method further comprising determining whether torque applied to the first member has exceeded the first level by at least the threshold amount of torque based at least in part on reception of the second photo-luminescent signal by the detector.

D0. A system comprising: a fastener including a first member configured for forceful engagement with a second member, the first member including a sensor configured to emit a first photo-luminescent signal indicating at least a first level of torque applied to the first member when the first and second members are engaged; and an inspection device configured to receive the first photo-luminescent signal from the sensor.

D1. The system of paragraph D0, wherein the inspection device is configured to determine the first level of torque by comparing spectral information included in the first photo-luminescent signal against a standard.

D2. The system of paragraph D0, wherein the inspection device is configured to determine whether the first level of torque has been reached based at least in part on reception of the first photo-luminescent signal.

D3. The system of paragraph D2, wherein the first level of torque corresponds with a desired level of torque for forceful engagement of the first member with the second member, the sensor being further configured to emit a second photo-luminescent signal indicating that torque applied to the first member has exceeded the first level by at least a threshold amount of torque, and the inspection device being further configured to determine whether torque applied to the first member has exceeded the first level by at least the threshold amount of torque based at least in part on reception of the second photo-luminescent signal.

D4. The system of paragraph D0, wherein the inspection device includes an emitter and a detector, the emitter being configured to emit electromagnetic radiation toward the sensor, the sensor being configured to emit the first photo-luminescent signal in response to absorption of the electromagnetic radiation from the emitter, the detector being configured to receive the first photo-luminescent signal from the sensor.

E0. A tool comprising: a tightening device configured to apply force to a first member engaged with a second member; and an inspection device coupled to the tightening device, the inspection device being configured to receive a photo-luminescent signal emitted from the first member, wherein the photo-luminescent signal indicates a level of force applied to the first member by the tightening device.

E1. The tool of paragraph E0, wherein the tightening device comprises a socket for receiving and torqueing a head portion of the first member, the photo-luminescent signal being received by the inspection device via the socket.

E2. The tool of paragraph E1, wherein the inspection device includes an emitter and a detector, the emitter being configured to emit electromagnetic radiation through the socket and toward a sensor included in the first member, the sensor being configured to emit the photo-luminescent signal in response to absorption of the electromagnetic radiation from the emitter, the detector being configured to receive the photo-luminescent signal from the sensor through the socket.

E3. The tool of paragraph E2, wherein the inspection device is configured to prevent the tightening device from further substantially forcefully engaging the first member with the second member based at least in part on reception of the photo-luminescent signal by the detector.

E4. The tool of paragraph E2, wherein the inspection device provides a signal to a user that indicates a level of force applied to the first member.

E5. The tool of paragraph E4, wherein the signal provided by the inspection device comprises an audible signal.

E6. The tool of paragraph E4, wherein the signal provided by the inspection device comprises a visual signal.

E7. The tool of paragraph E4, wherein the signal provided by the inspection device comprises a haptic signal.

F0. A washer comprising: a structural member having first and second opposing surfaces through which a central aperture is defined for receiving a shaft of a fastening member; and a sensor coated on one or more of the first and second surfaces, the sensor including a layer of polymer embedded with a fluorescent dye having a property that changes as a function of force applied to the structural member for emission of a photo-luminescent signal indicative of a level of force transmitted to the structural member by a head portion of the fastening member and another member through which the shaft extends opposite the head portion relative to the structural member.

G0. A system comprising: a fastener including a first member configured for forceful engagement with a second member, the first member including a sensor configured to emit a first luminescent signal indicating at least a first level of torque applied to the first member when the first and second members are engaged; and an inspection device configured to receive the first luminescent signal from the sensor.

G1. The system of paragraph G0, wherein the first luminescent signal is a photo-luminescent signal.

G2. The system of paragraph G0, wherein the first luminescent signal is a chemiluminescent signal.

G3. The system of paragraph G2, wherein the sensor includes first and second encapsulated chemical reactants configured to come into proximity to one another to form a chemiluminescent composition when the first level of torque is applied to the first member.

Advantages, Features, Benefits

The different embodiments described herein provide several advantages over known solutions for determining torque on a fastener. For example, the illustrative embodiments described herein allow for torque to be determined via an optical inspection of a sensor included in the fastener. However, not all embodiments described herein provide the same advantages or the same degree of advantage.

CONCLUSION

The disclosure set forth above may encompass multiple distinct embodiments with independent utility. Although each of these embodiments has been disclosed in its preferred form(s), the specific details of which as disclosed and illustrated herein are not to be considered in a limiting sense, because numerous variations are possible. The subject matter of the embodiments includes all novel and nonobvious combinations and subcombinations of the various elements, features, functions, and/or properties disclosed herein. The following claims particularly point out certain combinations and subcombinations regarded as novel and nonobvious. Embodiments of other combinations and subcombinations of features, functions, elements, and/or properties may be claimed in applications claiming priority from this or a related application. Such claims, whether directed to a different embodiment or to the same embodiment, and whether broader, narrower, equal, or different in scope to the original claims, also are regarded as included within the subject matter of the embodiments of the present disclosure.

What is claimed is:

1. A system comprising:
 a fastening device including a first member configured for forceful engagement with a second member, the first member including a sensor configured to emit a first photo-luminescent signal indicating at least a first level of torque applied to the first member when the first and second members are engaged, wherein the first member is a washer having a surface that is coated with the sensor, the washer contacting a surface of the second member when the washer and the second member are engaged; and
 an inspection device configured to receive the first photo-luminescent signal from the sensor.

2. The system of claim 1, wherein the inspection device is configured to determine the first level of torque by comparing spectral information included in the first photo-luminescent signal against a standard.

3. The system of claim 1, wherein the inspection device is configured to determine whether the first level of torque has been reached based at least in part on reception of the first photo-luminescent signal.

4. The system of claim 3, wherein the first level of torque corresponds with a desired level of torque for forceful engagement of the first member with the second member, the sensor being further configured to emit a second photo-luminescent signal indicating that torque applied to the first member has exceeded the first level by at least a threshold amount of torque, and the inspection device being further configured to determine whether torque applied to the first member has exceeded the first level by at least the threshold amount of torque based at least in part on reception of the second photo-luminescent signal.

5. The system of claim 1, wherein the inspection device includes an emitter and a detector, the emitter being configured to emit electromagnetic radiation toward the sensor, the sensor being configured to emit the first photo-luminescent signal in response to absorption of the electromagnetic radiation from the emitter, the detector being configured to receive the first photo-luminescent signal from the sensor.

6. The fastening device of claim 1, wherein the characterizing wavelength of a first photon corresponds to a wavelength of light that is non-visible to an unaided human eye.

7. The fastening device of claim 1, wherein the sensor is configured to emit a second photo-luminescent signal indicating when a predetermined second torque level is applied to the first member when the first and second members are engaged, the second torque level being greater than the first torque level, the sensor being further configured to emit a third photo-luminescent signal indicating when a predetermined third torque level is applied to the first member when the first and second members are engaged, the third torque level being less than the first torque level.

8. The fastening device of claim 1, wherein the second member is an object having an aperture for receiving the first member.

9. The fastening device of claim 1, wherein the detector includes a human eye.

10. The fastening device of claim 1, wherein the detector includes an electronic photo-detector configured to receive the first photo-luminescent signal, to generate a second signal based on and indicative of the first photo-luminescent signal, and to output the second signal to a user.

11. The fastening device of claim 1, wherein the first torque level is at least 3 foot-pounds.

* * * * *